(12) United States Patent
Perlmutter et al.

(10) Patent No.: US 9,511,074 B2
(45) Date of Patent: Dec. 6, 2016

(54) METHODS OF TREATING DISORDERS ASSOCIATED WITH PROTEIN POLYMERIZATION

(71) Applicant: UNIVERSITY OF PITTSBURGH—OF THE COMMONWEALTH SYSTEM OF HIGHER EDUCATION, Pittsburgh, PA (US)

(72) Inventors: David Hirsch Perlmutter, Pittsburgh, PA (US); George Konstantine Michalopoulos, Pittsburgh, PA (US); Tunde Hidvegi, Gibsonia, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 0 days.

(21) Appl. No.: 14/535,210

(22) Filed: Nov. 6, 2014

(65) Prior Publication Data

US 2015/0065488 A1 Mar. 5, 2015

Related U.S. Application Data

(63) Continuation of application No. 13/362,606, filed on Jan. 31, 2012, now Pat. No. 8,906,905, which is a continuation-in-part of application No. PCT/US2010/044243, filed on Aug. 3, 2010.

(60) Provisional application No. 61/230,921, filed on Aug. 3, 2009.

(51) Int. Cl.
*A61K 31/55* (2006.01)
*A61K 31/155* (2006.01)

(52) U.S. Cl.
CPC ............. *A61K 31/55* (2013.01); *A61K 31/155* (2013.01)

(58) Field of Classification Search
CPC .................................................. A61K 31/55
See application file for complete search history.

(56) References Cited

U.S. PATENT DOCUMENTS

| 5,658,900 | A | 8/1997 | Boireau et al. |
| 5,780,483 | A | 7/1998 | Widdowson et al. |
| 8,809,617 | B2 | 8/2014 | Pak et al. |
| 2003/0023997 | A1 | 1/2003 | Peraus et al. |
| 2003/0224508 | A1 | 12/2003 | Ill et al. |
| 2004/0213771 | A1 | 10/2004 | Sluder et al. |
| 2006/0079556 | A1 | 4/2006 | Sher et al. |
| 2006/0141625 | A1 | 6/2006 | Sisk et al. |
| 2007/0275957 | A1 | 11/2007 | Weiner et al. |
| 2009/0087916 | A1 | 4/2009 | Sato et al. |
| 2010/0076018 | A1 | 3/2010 | Liu et al. |
| 2010/0263062 | A1 | 10/2010 | Dillin et al. |
| 2011/0154510 | A1 | 6/2011 | Pak et al. |
| 2012/0129839 | A1 | 5/2012 | Perlmutter et al. |
| 2014/0047569 | A9 | 2/2014 | Pak et al. |
| 2014/0331341 | A1 | 11/2014 | Pak et al. |

FOREIGN PATENT DOCUMENTS

| CN | 101023944 | 8/2007 | |
| WO | WO 94/18972 | 9/1994 | |
| WO | WO 96/30766 | 10/1996 | |
| WO | WO 98/28971 | 7/1998 | |
| WO | WO 98/48784 | 11/1998 | |
| WO | WO 00/63427 A2 | 10/2000 | |
| WO | WO 00/73510 A1 | 12/2000 | |
| WO | WO 01/60840 A3 | 8/2001 | |
| WO | WO 02/096431 | 12/2002 | |
| WO | WO 2005/011610 | 2/2005 | |
| WO | WO 2008/030617 A2 | 3/2008 | |
| WO | WO 2008/092898 A1 | 8/2008 | |
| WO | WO 2008097924 A2 * | 8/2008 | ........... A61K 31/473 |
| WO | WO 2009/036275 | 3/2009 | |
| WO | WO 2009/039284 A1 | 3/2009 | |
| WO | WO 2009/049242 | 4/2009 | |
| WO | WO 2010085452 A1 * | 7/2010 | ............. A61K 31/11 |

OTHER PUBLICATIONS

U.S. Appl. No. 12/881,976, Jul. 7, 2014 Issue Fee payment.
U.S. Appl. No. 12/881,976, Apr. 11, 2014 Notice of Allowance.
U.S. Appl. No. 12/881,976, Nov. 25, 2013 Amendment and Request for Continued.
U.S. Appl. No. 12/881,976, Nov. 7, 2013 Advisory Action.
U.S. Appl. No. 12/881,976, Oct. 21, 2013 Response to Final Office Action.
U.S. Appl. No. 12/881,976, Jul. 19, 2013 Final Office Action.
U.S. Appl. No. 12/881,976, May 13, 2013 Response to Non-Final Office Action.
U.S. Appl. No. 12/881,976, Dec. 11, 2012 Non-Final Office Action.
U.S. Appl. No. 12/881,976, Aug. 13, 2012 Response to Restriction Requirement.
U.S. Appl. No. 12/881,976, Jul. 13, 2012 Restriction Requirement.
U.S. Appl. No. 13/362,606, Nov. 6, 2014 Issue Fee payment.

(Continued)

*Primary Examiner* — Samira Jean-Louis
(74) *Attorney, Agent, or Firm* — Baker Botts L.L.P.

(57) ABSTRACT

The present invention relates to methods of treatment of clinical disorders associated with protein polymerization comprising administering, to a subject, an effective amount of carbamazepine, oxcarbazepine or another carbamazepine-like compound. It is based, at least in part, on the discovery that, in cells having a genetic defect in α1-antitrypsin, carbamazepine was able to decrease levels of the mutant protein. Furthermore, carbamazepine reduced the hepatic load of mutant α1-antitrypsin and the toxic effect of that mutant protein accumulation, hepatic fibrosis, in vivo using a mouse model of the disease. As patients having this defect in α1-antitrypsin exhibit toxic accumulations of the protein, treatment according to the invention may be used to ameliorate symptoms and signs of disease.

4 Claims, 14 Drawing Sheets

(56) References Cited

OTHER PUBLICATIONS

Figure 1A:
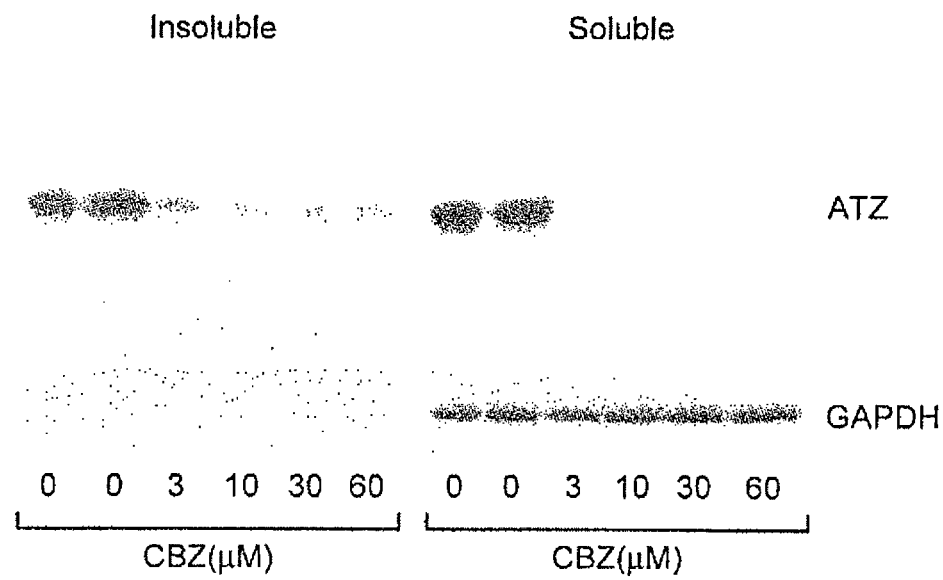

U.S. Appl. No. 13/362,606, Aug. 15, 2014 Notice of Allowance.
U.S. Appl. No. 13/362,606, Jun. 4, 2014 Response to Non-Final Office Action.
U.S. Appl. No. 13/362,606, Feb. 4, 2014 Non-Final Office Action.
U.S. Appl. No. 13/362,606, Dec. 6, 2013 Response to Restriction Requirement.
U.S. Appl. No. 13/362,606, Nov. 7, 2013 Restriction Requirement.
U.S. Appl. No. 13/463,638, Apr. 29, 2015 Notice of Allowance.
U.S. Appl. No. 13/463,638, Mar. 23, 2015 Response to Office Action.
U.S. Appl. No. 13/463,638, Dec. 29, 2014 Non-Final Office Action.
U.S. Appl. No. 13/463,638, Oct. 30, 2014 Notice of Appeal and Pre-Appeal Brief.
U.S. Appl. No. 13/463,638, Aug. 8, 2014 Advisory Action.
U.S. Appl. No. 13/463,638, Jul. 30, 2014 Response to Final Office Action.
U.S. Appl. No. 13/463,638, May 30, 2014 Final Office Action.
U.S. Appl. No. 13/463,638, May 13, 2014 Response to Non-Final Office Action.
U.S. Appl. No. 13/463,638, Nov. 22, 2013 Non-Final Office Action.
U.S. Appl. No. 13/463,638, Jun. 24, 2013 Response to Restriction Requirement.
U.S. Appl. No. 13/463,638, Jan. 23, 2013 Restriction Requirement.
Ambrósio, et al., "Neurotoxic/neuroprotective profile of carbamazepine, oxcarbazepine and two new putative antiepileptic drugs, BIA 2-093 and BIA 2-024", *Eur. J. Pharmacol.*, 406(2):191-201 (2000).
Arena, et al., "Huntington's Disease: Clinial Effects of a Short-Term Treatment with Pimozide", *Advances in Biochemical Psychopharmacology*, 24:573-575 (1980).
Bauer, et al., "Inhibition of Rho Kinases Enhances the Degradation of Mutant Huntingtin", *The Journal of Biological Chemistry*, 284(19):13153-13164 (2009).
Berger, et al., "Rapamycin alleviates toxicity of different aggregate-prone proteins", *Human Molecular Genetics*, 15(3):433-442 (2006).
Boland, et al., "Autophagy Induction and Autophagosome Clearance in Neurons: Relationship to Autophagic Patology in Alzheimer's Disease", *The Journal of Neuroscience*, 28(27):6926-6937 (2008).
Borowicz, et al., "Acute and Chronic Treatment with Mianserin Differentially Affects the Anticonvulsant Activity of Conventional Antiepileptic Drugs in the Mouse Maximal Electroshock Model", *Psychopharmacolgy*, 195(2):167-174 (2006).
Burton, et al., "Anaesthesia in Elderly Patients with Neurodegenerative Disorders—Special Considerations", *Drugs and Aging*, 21:229-242 (2004).
Cabral, et al., "Processing by Endoplasmic Reticulum Mannosidases Partitions a Secretion-impaired Glycoprotein into Distinct Disposal Pathways", *The Journal of Biological Chemistry*, 275(32):25015-25022 (2000).
Carlson, et al., "Multiple Tissues Express Alpha$_1$-Antitrypsin in Transgenic Mice and Man", *J. Clin. Invest.*, 82(1):26-36 (1988).
Carlson, et al., "Accumulation of PiZ $\alpha_1$-Antitrypsin Causes Liver Damage in Transgenic Mice", *J. Clin. Invest*, 83:1183-1190 (1989).
Chaudhuri et al., "Protein-misfolding diseases and chaperone-based therapeutic approaches", *FEBS Journal*, 273:1331-1349 (2006).
Cohen, et al., "Anti-Amyloid Effects of Small Molecule Aβ-Binding Agents in PS1/APP Mice", *Lett. Drug Des. Discov.*, 6(6):437 (2009).
Cohen, et al., "Reduced IGF-1 Signalling Delays Age-Associated Proteotoxicity in Mice", *Cell*, 139(6):1157-1169 (2009).
Cui, et al., "Role of glutathione in neuroprotective effects of mood stabilizing drugs lithium and valproate", *Neursocience*, 144(4):1447-1453 (2006).
Dollinger, et al., "A chimeric Ligand Approach Leading to Potent Antiprion Active Acridine Derivatives: Design, Synthesis, and Biological Investigations", *Journal of Medicinal Chemistry*, 49(22):6591-6595 (2006).

Feng, et al., "Small-molecule aggregates inhibit amyloid polymerization", *Nature Chemical Biology*, 4:197-199 (2008).
Filali, et al., "Age-related cognitive decline and nesting behavior in an APPswe/PS1 bigenic model of alzheimer's disease", *Brain Res.*, 1292:93-99 (2009).
Frey, et al., "Transient cholestatic hepatitis in a neonate associated with carbamazepine exposure during preganancy and breast-feeding", *Eur. J. Pediatr.*, 150(2):136-138 (1990).
Gao, et al., "Carbamazepine induction of apoptosis in cultured cerebellar neurons: effects of N-methyl-D-aspartate, aurintricarboxylic acid and cycloheximide", *Brain Res.*, 703(1-2):63-71 (1995).
Gong, et al., "Persistent improvement in synaptic and cognitive functions in an alzheimer mouse model after rolipram treatment", *The Journal of Clinical Investigation*, 114:1624-1634 (2004).
Gosai, et al., "Automated High-Content Live Animal Drug Screening Using C. elegans Expressing the Aggregation Prone Serpin $\alpha$1-Antitrypsin Z", *PLoS One*, 5(11):e15460 (2010).
Grant, et al., "Oxcarbazepine. a review of its pharmacology and therapeutic potential in epilepsy, trigeminal neuralgia and affective disorders", *Drugs*, 43(6):873-888 (1992).
Grieco, et al., "Fatty liver and drugs", *Eur Rev Med Pharmacol Sci.*, 9(5):261-263 (2005).
Haas, et al., "Soluble protein oligomers in neurodegeneration: lessons from the Alzheimer's amyloid beta-peptide", *Nat. Rev. Mol. Cell Biol.*, 8(2):101-112 (2007).
Harada, et al., "Autophagy Activation by Rapamycin Eliminates Mouse Mallory-Denk Bodies and Blocks Their Proteasome Inhibitor-Mediated Formation", *Hepatology*, 47(6):2026-2035 (2008).
Hidvegl, et al., An Autophagy-Enhancing Drug Promotes Degradation of Mutant $\alpha_1$-antitrypsin Z and Reduces Hepatic Fibrosis, *Science*, 329:229-232 (2010).
Hidvegl, et al., "Regulator of G signalling 16 is a marker for the distinct endoplasmic reticulum stress state associated with aggregated mutant $\alpha_1$-antitrypsin Z in the classical form of $\alpha_1$-antitrypsin deficiency", *The Journal of Biological Chemistry*, 282(38):27769-27780 (2007).
Hidvegl, et al., "Accumulation of Mutant $\alpha_1$-Antitrypsin Z in the Endoplasmic Reticulum Activates Caspases-4 and -12, NFκB, and BAP31 but not the Unfolded Protein Response", *The Journal of Biological Chemistry*, 280(47):39002-39015 (2005).
Holcomb, et al., "Behavioral changes in transgenic mice expressing both amyloid precursor protein and presenilin-1 mutations: lack of association with amyloid deposits", *Behav. Genet.*, 29(3):177-185 (1999).
Hosokawa, et al., "Generation of cell lines with tetracycline-regulated autophagy and a role for autophagy in controlling cell size", *FEBS Letters*, 580(11):2623-2629 (2006).
International Search Report for PCT/US2010/044243, dated Sep. 30, 2010.
International Search Report for PCT/US2010/002898, dated Jan. 31, 2011.
Juruena, et al., "Bipolar I and II disorder residual symptoms: oxcarbazepine and carbamazepine as add-on treatment to lithium in a double-blind, randomized trial", *Prog. Neuropsychopharmacol Biol. Psychiatry*, 33(1):94-99 (2009).
Kamimoto, et al., "Intracellular inclusions containing mutant alpha1-antitrypsin Z are propagated in the absence of autophagic activity", *The Journal of Biological Chemistry*, 281(7):4467-4476 (2006).
Kirkin, et al., "A role for ubiquitin in selective autophagy", *Mol. Cell.*; 34(3):259-269 (2009).
Korenyi, et al., "Drug Treatment in 117 Cases of huntington's Disease with Special Reference to Fluphenazine (Prolixin)", *Psychiatric Quarterly*, 41:203-210 (1967).
Kruse, et al., "Characterization of an ERAD Gene as VPS30/ATG6 Reveals Two Alternative and Functionally Distinct Protein Quality Control Pathways: One for Soluble Z Variant of Human $\alpha$-1 Proteinase Inhibitor (A1PiZ) and Another for Aggregates of A1PiZ", *Molecular Biology of the Cell*, 17(1):203-212 (2006).

(56) References Cited

OTHER PUBLICATIONS

Lawless et al., "Endoplasmic reticulum stress—A double edged sword for Z alpha-1 antitrypsin deficiency hepatoxicity", *The International Journal of Biochemistry & Cell Biology*, 40:1403-1414 (2008).
Lee, et al., "Protein Folding and Diseases", *Journal of Biochemistry and Molecular Biology*, 38:275-280 (2005).
Lin, et al., "A Naturally Occuring nonpolymerogenic Mutant of $\alpha$1-Antitrypsin Characterized by Prolonged Retention in the Endoplasmic Reticulum", *The Journal of Biological Chemistry*, 276(36):33893-33898 (2001).
Loberts, et al., "Additivity of Dilantin and Vinblastine Inhibitory Effects on Microtubule Assembly", *Cancer Research*, 59(19):4816-4822 (1999).
Lomas, et al., "The mechanism of Z alpha 1-antitrypsin accumulation in the liver", *Nature*, 357(6379):605-607 (1992).
Luef, et al., "Non-alcoholic fatty liver disease (NAFLD), insulin resistance and lipid profile in antiepileptic drug treatment", *Epilepsy Res.*, 86(1):42-47 (2009).
Maeda, et al., "IKK$\beta$ is required for prevention of apoptosis mediated by cell-bound but not by circulating TNF$\alpha$", *Immunity*, 19(5):725-737 (2003).
Mizushima, et al., "How to Interpret LC3 Immunoblotting", *Autophagy*, 3(6):542-545, (2007).
Mizushima, et al., "Autophagy fights disease through cellular self-digestion", *Nature*, 451(7182):1069-1075 (2008).
Naisbitt, et al., "Hypersensitivity Reactions to carbamazepine: Characterization of the Specificity, Phenotype, and Cytokine Profile of Drug-Specific T Cells Clones", *Molecular Pharmacology*, 63(3):732-741 (2003).
Nixon, "Autophagy, amyloidogenesis and Alzheimer diease", *Journal of Cell Science*, 120(Pt 23):4081-4091 (2007).
Österreicher, et al., "Angiotensin-Converting-Enzyme 2 Inhibits Liver Fibrosis in Mice", *Hepatolgy*, 50:929-938 (2009).
Oury, et al., "Attenuation of Bleomycin-Induced Pulmonary Fibrosis by a Catalytic Antioxidant Metalloporphyrin", *Am. J. Respir. Cell Mol. Biol.*, 25(2):164-169 (2001).
Pan, et al., "SNP-mediated translational suppression of ERMan1 modifies the onset of end-stage liver disease in alpha1-antitrypsin defiency", *Hepatology*, 50(1):275-281 (2009).
Paranjpe, et al., "Cell cycle effects resulting from inhibition of hepatocyte growth factor and its receptor c-Met in regenerating rat livers by RNA interference", *Hepatology*, 45(6):1471-1477 (2007).
Perlmutter et al., FASEB Summer Research Conferences, From unfolded proteins in the endoplasmic reticulum to disease, "Acummulation of an aggregation-prone protein in the ER causes liver disease in $\alpha$1-antitrypsin deficiency", Abstract, (Jun. 7-12, 2009).
Perlmutter, ., "Accumulation of an aggregation-prone mutant protein in the endoplasmic reticulum causes liver disease in alpha-1-antitrypsin deficiency: The role of autophagy and other intracellular disposal pathways", Presentation, National Institute of Diabetes & Digestive and Kidner Diseases Workshop, Bethesda, MD, Jan. 29, 2009.
Perlmutter, "Alpha-1 antitrypsin deficiency: an Aggregation-prone protein causes childhood liver disease". Presentation, Howard Rappaport Memorial Lecture, Pediatric Grand Rounds, Mt. Sinai School of Medicine, New York, NY, Feb. 26, 2009.
Perlmutter, "Alpha-1-Antitrypsin Deficiency: Liver Inflammation and Carcinoma from Aggregation-prone Protein," Presentation, Pediatric Grand Rounds, University of California, San Diego, CA, Mar. 19, 2009.
Perlmutter, "Alpha-1-Antitrypsin Deficiency: Childhood Liver Disease from an Aggregation-prone Protein," Presentation, Pediatric Grand Rounds, Children's Hospital, Boston, MA, May 20, 2009.
Perlmutter, "Autophagic Disposal of the Aggregation-Prone Protein that Causes Liver Inflammation and Carcinogenesis in $\alpha$-1-antitrypsin Deficiency", *Cell Death and Differentiation*, 16(1):39-45 (2009).

Perlmutter, et al., "The role of autophagy in Alpha-1-Antitrypsin deficiency: A specific cellular response in genetic diseases associated with aggregation-prone proteins", *Autophagy*, 2(4):258-263 (2006).
Pickford, et al., "The autophagy-related protein beclin 1 shows reduced expression in early Alzheimer disease and regulates amyloid $\beta$ accumulation in mice", *The Journal of Clinical Investigation*, 118(6):2190-2199 (2008).
Piitulainen, et al., "Alpha1-antitrypsin deficiency in 26-year-old sugjects: lung, liver, and protease/protease inhibitor studies", *Chest.*, 128(4):2076-2081 (2005).
Powers, et al., "Biological and Chemical Approaches to Diseases of Proteostasis Defiency", *Annual Review of Biochemistry*, 78:959-991 (2009).
Qu, et al., "Degradation of a Mutant Secretory Protein, $\alpha_1$-antitrypsin Z, in the Endoplasmic Reticulum Requires Proteasome Activity", *The Journal of Biological Chemistry*, 271(37):22791-22795 (1996).
Ramirez, et al., "Prevention of Alzheimer's Disease Pathology by Cannabinoids: Neuroprotection Mediated by Blockade of Microglial Activation", *The Journal of Neuroscience*, 25:1904-1913 (2005).
Ravikumar, et al., "Clearance of mutant aggregate-prone proteins by autophagy", *Methods Mol. Biol.*, 445:195-211 (2008).
Rudnik, et al., "Analyses of hepatocellular proliferation in a mouse model of alpha-1-antitrypsin deficiency", *Hepatology*, 39(4):1048-1055 (2004).
Sarkar,et al., "Lithium induces autophagy by inhibiting inositol monophosphatase", *The Journal of Cell Biology*, 170(7):1101-1111 (2005).
Sarkar, et al., "Small molecules enhance autophagy and reduce toxicity in Huntington's disease models", *Nat. Chem Biol.*; 3(6):331-338 (2007).
Schmidt, et al., "Grp78, Grp94, and Grp170 interact with $\alpha$1-antitrypsin mutants that are reatined in the endoplasmic reticulum", *Am J. Physiol Gastrointest Liver Physiol.*, 289:G444-G455 (2005).
Seki, et al., "CCR2 Promotes Hepatic Fibrosis in Mice", *Hepatology*, 50:185-197 (2009).
Sifers, "Medicine. Clearing conformational disease", *Science*, 329(5988):154-155 (2010).
Stepanović-Petrović, et al., "The Antinociceptive Effects of anticonvulsants in a Mouse Visceral Pain Model", *Anesthesia & Analgesia*, 106(6):1897-1903 (2008).
Strang, "Imipramine in treatment of Parkinsonism: A double-Blind Placebo Study", *British Medical Journal*, 2(5452):33-34 (1965).
Teckman, et al., "Mitochondrial autophagy and injury in the liver in $\alpha_1$-antitrypsin defiency", *Am J Physiol Gastrointest Liver Physiol*, 286(5):G851-G862 (2004).
Teckman, et al., "Retention of mutant $\alpha_1$-antitrypsin Z in endoplasmic reticulum is associated with an autophagic response", *Am J Physiol Gastrointest Liver Physiol*, 279(5):G961-G974 (2000).
Teckman, et al., "Fasting in $\alpha_1$-antitrypsin deficient liver: constitutive activation of autophagy", *Am J Physiol Gastrointest Liver Physiol*, 283(5):G1156-G1165 (2002).
Wu, et al., "A lag in intracellular degradation of mutant $\alpha$1-antitrypsin correlates with the liver disease phenotype in homozygous PiZZ $\alpha$1-antitrypsin deficiency", *PNAS*, 91(19):9014-9018 (1994).
Zhang, et al., "Small molecule regulators of autophagy identified by an image-based high-throughput screen", *PNAS*, 104(48):19023-19028 (2007).
Zhang, et al., "Microtubule-binding drugs offset tau sequestration by stabilizing microtubules and reversing fast axonal transport deficits in a tauopathy model", *Proceedings of the National Academy of Sciences*, 102:227-231 (2005).
U.S. Appl. No. 14/728,619 (US 2015/0265626), filed Jun. 2, 2015 (Sep. 24, 2015).
U.S. Appl. No. 14/728,619, May 25, 2016, Notice of Allowance.
U.S. Appl. No. 14/728,619, Mar. 18, 2016, Response to Non-Final Office Action.
U.S. Appl. No. 14/728,619, Mar. 18, 2016, Terminal Disclaimer Filed.

(56) References Cited

OTHER PUBLICATIONS

U.S. Appl. No. 14/728,619, Nov. 18, 2015, Non-Final Office Action.
Balch et al., "Adapting proteostasis for disease intervention", Science, Feb. 15, 2008, vol. 319: 916-919.
Bleicher et al., "Hit and lead generation: Beyond high-throughput screening", Nature Reviews, May 2003, vol. 2: 369-378.
Bossle et al., "Synthesis and Biological Activity of New 2-Substituted Analogs of Fluphenazine", J Med Chem. 19(3), 370-373 (1976).
Breger et al., "Anti-fungal chemical compounds indentified using a C. elegans pathogenicity assay", PloS Pathogens, Feb. 2007, 3(2) e18: 0168-0178.
Brideau et al., "Improved statistical methods for hit selection in high-throughput screening", The Society for Biomolecular Screening, 2003, 8(6): 634-647.
Chao et al., "Structure-guided synthesis of tamoxifen analogs with improved selectivity for the orphan ERRγ", Bioorg. Med Chem. Lett. 16(4), 821-824 (2006).
Driscoll et al., "The mec-4 gene is a member of a family of Caenorhabditis elegans genes that can mutate to induce neuronal degeneration", Nature, Feb. 14, 1991, vol. 349: 588-593.
Dycaico et al., "Neonatal hepatitis induced by a1-Antitrypsin: A transgenic mouse model", Science, Dec. 9, 1988, vol. 242: 1409-1412.
Ellerbrock et al., "Screening for presenilin inhibitors using the free-living nematode, Caenorhabditis elegans", The Society for Biomolecular Screening, 2004, 9(2): 147-152.
Faber et al., "Polyglutamine-mediated dysfunction and apoptotic death of a Caenorhabditis elegans sensory neuron", Proc. Natl. Acad Sci. USA, Jan. 1999, vol. 96: 179-184.
Frearson et al., "HTS and hit finding in academia—from chemical genomics to drug discovery", Drug Discovery Today, Dec. 2009, 14(23/24): 1150-1158.
Giuliano et al., "Advances in high content screening for drug delivery", ASSAY and Drug Development Technologies, 2003, 1(4): 565-577.
Gleeson et al., "ADMET rules of thumb II: A comparison of the effects of common substituents on a range of ADMET parameters", Bioorganic & Medicinal Chemistry, 2009, vol. 17: 5906-5919.
Gleeson, "Generation of a set of simple, interpretable ADMET rules of thumb", J Med Chem., 2008, vol. 51: 817-834.
Grover et al., "Differential Effects of Paclitaxel (Taxol) Analogs Modified at Positions C-2, C-7, and C-3' on Tubulin Polymerization and Polymer Stabilization: Identification of a Hyperactive Paclitaxel Derivative", Biochemistry 34, 3927-3934 (1995).
Haney et al., "High-content screening moves to the front of the line†", Drug Discovery Today, Oct. 2006, 11 (19/20): 889-894.
Hirata et al., "Potential CNS Antitumor Agents-Phenothiazines II: Fluphenazine Analogs" J Pharm. Sci. 67(2), 157-162 (1978).
Hodgson, "ADMET-turning chemicals into drugs", Nature Biotechnology, Aug. 2001, vol. 19: 722-726.
Hoffner et al., "Protein Aggregation in Huntington's Disease", Biochimie, 84:273-278 (2002).
Johnston et al., "Cdc25B dual-specificity phosphatase inhibitors identified in a high throughput screen of the NIH compound library", ASSAY and Drug Development Technologies, Jun. 2009, 7(3): 250-265.
Johnston et al., "Development and implementation of a 384-Well homogeneous fluorescence intensity high-throughput screening assay to identify mitogen-activated protein kinase phosphatase-I dual-specificity protein phosphatase inhibitors", ASSAY and Drug Development Technologies, 2007, 5(3): 319-332.
Johnston et al., "Development of a 384-Well colorimetric assay to quantify hydrogen peroxide generated by the redox cycling of compounds in the presence of reducing agent", Assay and Drug Development Technologies, 2008, 6(4): 505-518.
Johnston et al., "HTS identifies novel and specific uncompetitive inhibitors of the twocomponent NS2B-NS3 proteinase of west Nile virus", ASSAY and Drug Development Technologies, 2007, 5(6): 737-750.
Kang et al., "Dual roles of autophagy in the survival of Caenorhabditis elegans during starvation", Genes and Development, 2007, vol. 21: 2161-2171.
Kok et al., "Induction of apoptosis on carcinoma cells by two synthetic cantharidin analogues", Int. J Mal. Med 17(1), 151-157 (2006).
Kopito et al., "Conformational Disease", Nature Cell Biology, 2:E207-E209 (2000).
Kwok et al., "A small-molecule screen in C. elegans yields a new calcium channel antagonist", Nature, May 2006, vol. 441: 91-95.
Lee et al., "High-content screening: Emerging hardware and software technologies", Methods in Enzymology, 2006, vol. 414: 468-483.
Link, "Expression of human β-amyloid peptide in transgenic Caenorhabditis elegans", Proc. Natl. Acad Sci. USA, Sep. 1995, vol. 92: 9368-9372.
Luke et al., "An intracellular serpin regulates necrosis by inhibiting the induction and sequelae of lysosomal injury", Cell, Sep. 21, 2007, vol. 130: 1108-1119.
Lum et al., "Autophagy in metazoans: Cell survival in the land of plenty", Nature Reviews/Molecular Cell Biology, Jun. 2005, vol. 6: 439-448.
Malo et al., "Statistical practice in high-throughput screening data analysis", Nature Biotechnology, Feb. 2006, 24(2): 167-175.
Martin et al., "Therapeutic perspectives for the treatment of Huntington's disease: Treating the whole body", Histol Histopathol., 23(2):237-250 (2008).
Mayr et al., "Novel trends in high-throughput screening", Current Opinion in Pharmacology, 12009, vol. 9: 580-588.
McCluskey et al., "The First Two Cantharidin Analogues Displaying PP1 Selectivity", Bioorganic & Medicinal Chemistry Letters 12(3):391-393 (2002).
Melendez et al., "Autophagy Genes Are Essential for Dauer Development and Life-Span Extension in C. elegans", Science, Sep. 5, 2003, vol. 301: 1387-1391.
Molina et al., "Zebrafish chemical screening reveals an inhibitor of Dusp6 that expands cardiac cell lineages", Nature Chemical Biology, Sep. 2009, 5(9): 680-687.
Morley et al., "The threshold for polyglutamine-expansion protein aggregation and cellular toxicity is dynamic and influenced by aging in Caenorhabditis elegans", PNAS, Aug. 6, 2002,99(16): 10417-10422.
Moy et al., "High-throughput screen for novel antimicrobials using a whole animal infection model", ACS Chemical Biology, 2009, 4(7): 527-533.
Moyna et al., "Conformational Studies of Paclitaxel Analogs Modified at the C-2' Position in Hydrophobic and Hydrophilic Solvent Systems", J Med Chem. 40(20), 3305-3311 (1997).
Nehrke et al., "The NHX family of Na+-H+ exchangers in Caenorhabditis elegans", The Journal of Biological Chemistry, Aug. 9, 2002, 277(32): 29036-29044.
Nehrke, "A reduction in intestinal cell pHi due to loss of the Caenorhabditis elegans Na+/W exchanger NHX-2 increases life span", The Journal of Biological Chemistry, Nov. 7, 2003, 278(45): 44657-44666.
North et al., "Prostaglandin E2 regulates vertebrate haematopoietic stem cell homeostasis", Nature, Jun. 21, 2007, vol. 447: 1007-1011.
Okoli et al., "Identification of antifungal compounds active against Candida albicans using an improved high-throughput Caenorhabditis elegans Assay", PloS ONE, Sep. 2009, 4(9) e7025: 1-8.
Parmar et al., "Alpha-1-antitrypsin deficiency, the serpinopathies and conformational disease", JR Coll Physicians Land, 34(3):295-300 (2000) (Abstract only).
Perlmutter, "Liver injury in a α1-antitrypsin deficiency: an aggregated protein induces mitochondrial injury", J Clin. Invest., 2002, vol. 110: 1579-1583.
Petrascheck et al., "An antidepressant that extends lifespan in adult Caenorhabditis elegans", Nature, Nov. 22, 2007, vol. 450: 553-556.
Rihel et al., "Zebrafish behavioral profiling links drugs to biological targets and rest/wake regulation", Science, Jan. 15, 2010, vol. 327: 348-351.

(56) References Cited

OTHER PUBLICATIONS

Royal et al., "Temperature-sensitive mutant of the Caenorhabditis elegans neurotoxic MEC-4(d) DEG/EnaC channel identifies a site required for trafficking or surface maintenance", The Journal of Biological Chemistry, Dec. 23, 2005, 280(51): 41976-41986.

Silverman et al., "Modeling molecular and cellular aspects of human disease using the nematode Caenorhabditis elegans", Pediatric Research, 2009, 65(1): 10-18.

Stockwell, "Chemical genetics: Ligand-based discovery of gene function", Nature Reviews/Genetics, Nov. 2000, 1(2): 116-125.

Stoller et al., "α1-antitrypsin deficiency", Lancet, Jun. 25-Jul 1, 2005: 365(9478): 2225-2236.

Szewczyk et al., "Chemically defined medium and Caenorhabditis elegans", BMC Biotechnology, 2003, 3, 19-eoa.

Thaqi et al., "Synthesis and biological activity of Δ-5,6-norcantharimides: importance of the 5,6-bridge", Eur. J Med Chem. 45(5), 1717-1723 (2010).

Tran et al., "Automated, quantitive screening assay for antiangiogenic compounds using transgenic zebrafish", Cancer Research, Dec. 1, 2007, 67(23): 11386-11392.

Walker et al., "Molecular cloning and heterologous expression of the C-13 phenylpropanoid side chain-CoA acyltransferase that functions in Taxol biosynthesis" Proc. Natl. Acad Sci. USA. 99(20), 12715-12720 (2002).

Werner et al., "Proteasome-dependent endoplasmic reticulum-associated protein degradation: An unconventional route to a familiar fate", Proc. Natl. Acad. Sci. USA, Nov. 1996, vol. 93: 13797-13801.

Williams et al., "Novel targets for Huntington's disease in an mTOR-independent autophagy pathway", Nature Chemical Biology, May 2008, 4(5): 295-305.

Yu et al., "Dorsomorphin inhibits BMP signals required for embryogenesis and iron metabolism", Nature Chemical Biology, Jan. 2008, 4(1): 33-41.

Zhang et al., "A simple statistical parameter for use in evaluation and validation of high throughput screening assays", Journal of Biomolecular Screening, 1999, 4(2): 67-73.

\* cited by examiner 0  2.5  5  10  50  100 200
CBZ (μM)

CBZ 0  60 120 180 240 300    0  60 120 180 240 300
        IC                        EC
              Control 0  60 120 180 240 300  0  60 120 180 240 300
        IC                       EC

| | SMA | Col1A | TGFβ1 |
|---|---|---|---|
| Control | 1.585 + 0.423 | 2.082 + 0.605 | 0.531 + 0.049 |
| CBZ | 0.685 + 0.096 | 1.235 + 0.232 | 0.440 + 0.041 |
| p | 0.035 | 0.20 | 0.17 |

METHODS OF TREATING DISORDERS ASSOCIATED WITH PROTEIN POLYMERIZATION

PRIORITY CLAIM

This application is a continuation of U.S. patent application Ser. No. 13/362,606 filed Jan. 31, 2012 which is a continuation-in-part of International Patent Application No. PCT/US2010/044243 filed Aug. 3, 2010 which claims priority to U.S. Provisional Patent Application No. 61/230,921 filed Aug. 3, 2009, to each of which priority is claimed and the contents of each of which are incorporated by reference in their entireties herein.

GRANT INFORMATION

This invention was made with government support under grants HL037784 and DK076918 awarded by the National Institutes of Health. The government has certain rights in the invention.

1. INTRODUCTION

The present invention relates to methods of treatment of clinical disorders associated with protein polymerization comprising administering, to a subject, an effective amount of carbamazepine ("CBZ"), oxcarbazepine ("OBZ") or another carbamazepine-like compound.

2. BACKGROUND OF THE INVENTION

The classical form of α1-antitrypsin ("AT") deficiency is an autosomal co-dominant disorder that affects approximately 1 in 2000 live births (25). It is caused by a point mutation that alters the folding of an abundant liver-derived plasma glycoprotein during biogenesis and also renders it prone to polymerization (43). In addition to the formation of insoluble aggregates in the ER of liver cells, there is an 85-90% reduction in circulating levels of AT, the predominant physiologic inhibitor of neutrophil elastase. Individuals who are homozygous for the mutant allele are susceptible to premature development of chronic obstructive pulmonary disease. Pulmonary involvement is believed to be caused by a loss-of-function mechanism, as lack of AT in the lung permits elastase to slowly destroy the pulmonary connective tissue matrix (44).

AT deficiency is the most common genetic cause of liver disease in children and also causes liver disease and hepatocellular carcinoma in adults. In contrast to pulmonary involvement, liver inflammation and carcinogenesis are believed to be caused by a gain-of-toxic function mechanism. This is most clearly demonstrated by introducing the mutant human ATZ allele as transgene into genetically engineered mice (45, 11). Insoluble aggregates in hepatocytes, hepatic inflammation and carcinogenesis evolve even though the endogenous anti-elastases of the transgenic mouse are intact.

Cohort studies from an unbiased Swedish newborn screening program have shown that only 8-10% of the affected homozygous population develop clinically significant liver disease through the first 30 years of life (26). This has led to the concept that genetic and/or environmental modifiers determine whether an affected homozygote is susceptible to, or protected from, liver disease. Furthermore, it has led to consideration of two general explanations for the effects of such modifiers: variation in the function of intracellular degradative mechanisms and/or variation in the signal transduction pathways that are activated to protect the cell from protein mislocalization and/or aggregation.

Studies in this area have so far indicated that the proteasome is responsible for degrading soluble forms of ATZ (29, 46) and that macroautophagy is specialized for disposal of the insoluble polymers/aggregates that accumulate in the ER (30, 47). In terms of cellular response pathways, it is thought that accumulation of ATZ activates NFκB and autophagy but not the unfolded protein response (1, 16).

Polymerization of protein is associated with a number of other disorders. Among these is Alzheimer's Disease ("AD"), a disorder which affects four million people in the United States and has an incidence estimated at 1 in 68 individuals. As such, AD is the most common form of age-dependent neurodegeneration. Most cases are recognized by the sporadic onset of dementia during the seventh decade of life while the less common, mutation-linked familial cases cause dementia that is recognized by the fifth decade. AD is associated with the accumulation of aggregation-prone peptides in the brain, especially amyloid-β ("Aβ") peptides, but hyperphosphorylated tau proteins also contribute to the tangles and plaques that constitute the histological hallmarks of the disease.

AD is thought to be caused by a gain-of-toxic function mechanism that is triggered by the accumulation of aggregated Aβ and tau and worsened by aging (36). Recent studies have shown that the prevalence of autophagosomes is increased in dystrophic neurons of the AD brain, a finding that is recapitulated in mouse models of the disease (37). Most of the evidence suggests that autophagy plays a role in disposal of aggregated proteins that might have toxic effects on neurons (38, 39). In fact, the neuropathological effects of Aβ in a mouse model of AD were ameliorated by enhancing autophagy via overexpression of the autophagy protein beclin 1 (39). In a study by Cohen et al., breeding of a mouse model of AD to a mouse model with targeted disruption of the IGF-1 receptor demonstrated that reduced IGF-1 signaling blunted and delayed the toxic effect of Aβ accumulation (40). Although this could be attributed in part to sequestration of soluble Aβ oligomers into dense aggregates of lower toxicity, it is well established that IGF-1 signaling inhibits autophagy and therefore that these mice would likely have enhanced autophagy. Thus, based on the current literature, autophagy may be increased in AD, but the load of oligomers may be too great to avoid toxic Aβ accumulation.

Other disorders associated with increased protein aggregates include Parkinson's Disease and Huntington's Chorea. Parkinson's Disease is associated with the presence of protein aggregates in the form of "Lewy Bodies", which contain a number of proteins including one or more of alpha-synuclein, ubiquitin, neurofilament protein, alpha B crystallin and tau protein. Interestingly, a number of other disorders manifested as dementia are also associated with the presence of Lewy Bodies in neurons—these include Alzheimer's Disease, Pick's Disease, corticobasal atrophy, multiple system atrophy, and so-called "dementia with Lewy Bodies" or "DLB". Huntington's Chorea is associated with aggregates of huntingtin protein containing a mutation that results in long tracts of polyglutamine ("polyQ") which result in improper protein processing and aggregate formation.

Carbamazepine ("CBZ"; also known as Tegretol®, Carbatrol, and Equetro), is a drug that has been used for many years as an anticonvulsant in the treatment of epilepsy and as a specific analgesic for treatment of trigeminal neuralgia. It is believed to act by reducing post-synaptic responses and blocking post-tetanic potentiation in the nervous system. CBZ is known to increase hepatic cytochrome P450 activity and thereby affect the clearance of other pharmaceuticals eliminated through that system. It is metabolized in the liver (see Prescribing Information from Novartis Pharmaceuticals).

Oxcarbazepine ("OBZ", also known as Trileptal®) is, like CBZ, a drug used in the treatment of seizures and trigeminal neuralgia; in addition, it is used as a mood stabilizer. Unlike CBZ, neither OBZ nor its monohydroxy derivative induce hepatic oxidative metabolism (with the possible exception of P450IIIA isozyme (58).

3. SUMMARY OF THE INVENTION

The present invention relates to methods of treatment of clinical disorders associated with protein polymerization comprising administering, to a subject, an effective amount of carbamazepine or a carbamazepine-like compound. It is based, at least in part, on the discoveries that CBZ could decrease steady state levels of ATZ protein in cells and animals manifesting the ATZ mutation, and was observed to decrease the amount of ATZ accumulated in the liver in a mouse model of AT deficiency, and that OBZ was able to decrease the cellular ATZ load at lower doses than CBZ. According to the invention, treatment with CBZ, OBZ or a similar compound may therefore be used to ameliorate the symptoms and signs of AT deficiency as well as other disorders marked by protein polymerization, including, but not limited to, Alzheimer's Disease, Parkinson's Disease, and Huntington's Disease.

Without being bound by any particular theory, it appears that CBZ lowers ATZ, levels by not only increasing autophagy, but also by increasing proteasomal degradation of ATZ as well as by another mechanism outside the lysosomal and proteosomal systems.

4. BRIEF DESCRIPTION OF THE FIGURES

FIG. 1A-D. (A) Effect of CBZ on steady state levels of ATZ in the HTO/Z cell line. Immunoblot analysis of HTO/Z cells treated with different concentrations of CBZ, separated into soluble and insoluble fractions and then probed with antibodies to AT (top) and GAPDH (bottom). (B) Effect of CBZ and rapamycin (RAP) on steady state levels of ATZ in the HTO/Z cell line. After a 48-hour incubation in CBZ or RAP in the concentrations indicated at the bottom of the figure, cells were homogenized, cell homogenates separated into insoluble and soluble fractions and these fractions were then subjected to immunoblot analysis for AT (top) and GAPDH (bottom). (C) Effect of different concentrations of CBZ on steady state levels of ATZ in the HTO/Z cell line. Densitometric results from 8 different experiments are plotted on the vertical axis and concentration of CBZ on the horizontal axis. The number of samples at each concentration is indicated just above the horizontal axis. Results for the insoluble fraction are shown on the left and for the soluble fraction on the right. Results are expressed as mean+/−SD. (D) Effect of CBZ on steady state levels of wild type AT in the HTO/M cell line and on steady state levels of BiP in the HTO/Z cell line. This was carried out as in FIG. 1B.

FIG. 2A-D. Effect of CBZ on synthesis (A) and kinetics of secretion (B, C) of ATZ in the HTO/Z cell line. (A) Cell lysates after pulse labeling were immunoprecipitated with anti-AT; (B) Cell lysates (IC) and extracellular fluid (EC) were immunoprecipitated with anti-AT after pulse-chase labeling. (C) Kinetics of disappearance from IC was determined by densitometric scanning of fluorograms from 5 separate experiments. Data is shown as mean+/−standard error. Dashed lines show the half-time for disappearance. (D) Effect of CBZ on the fate of ATZ in pulse-chase analysis. Fluorographic images from 5 separate pulse-chase experiments described in FIGS. 2B and 2C were subjected to densitometric scanning. In contrast to FIG. 2C the data from both intracellular and extracellular contents are displayed in a histogram. The relative densitometric intensity of the AT band at T0 IC is set at 100% and every other band is compared to that. The relative amount IC is shown in white and EC as hatched. The results for control are shown on the left and CBZ on the right. Using this display it can be seen that in CBZ-treated cells there is an increase in the rate of disappearance of ATZ from the IC, a decrease in the amount of ATZ that appears in the EC, and a decrease in the amount of ATZ recovered from IC and EC together. Together, this data demonstrates that the effect of CBZ is solely an enhancement of ATZ degradation—i.e. CBZ does not affect secretion.

FIG. 3A-F. (A) Effect of CBZ on LC3 conversion in the HTO/Z cell line by immunoblot. Densitometric values are shown at the bottom. (B and C) Effect of CBZ on ATZ in autophagy-deficient (Atg5−/−) (B) versus wild-type (Atg5+/+) (C) cell lines. (D) Effect of CBZ on levels of the AT Saar variant in the HTO/Saar cell line compared to ATZ in the HTO/Z line. (E) Effect of CBZ on ATZ levels in the presence of proteasomal inhibitors. For the last 6 hours of incubation with CBZ (30 mM) or control, proteasomal inhibitors were added to some of the monolayers. The experiments were done as in FIG. 1A. For loading control, immunoblots for GAPDH are shown in the lower panels. Similar results were obtained in three separate experiments. (F) Effect of inducing expression of AT on LC3 conversion in HTO/Z (Z, left panel) and HTO/Saar (Saar, right panel) cell lines. Each cell line was incubated in the absence or presence of doxycycline (DOX) for 4 weeks. Separate monolayers that were incubated in the absence or presence of dox were incubated with lysosomal protease inhibitors (Lys. inh.), E64d (20 µg/ml) and pepstatin A (20 µg/ml), for the last 4 hours prior to harvesting and homogenization. These homogenates were subjected to immunoblot analysis for LC3. Densitometric values for the LC3-II/LC3-I ratio are also shown, with the relative densitometric value in the presence of DOX but not Lys inh arbitrarily set as 1.0. The results show that there is an increase in the LC3-II to LC3-I ratio when dox is removed in the Z cell line (compare lanes 3 and 4 to lanes 1 and 2) and this is further increased in the presence of lysosomal inhibitors (compare lanes 7 and 8 to 5 and 6; it will also help to compare lanes 5-8 to lanes 1-4). This LC3 conversion is specific for Z as shown by the results of inducing Saar. There is no increase in LC3 II when dox is removed in the Saar cell line (compare lane 10 to 9) and no change when lysosomal inhibitors are added (lane 11). These results are representative of 3 separate experiments.

FIG. 4A-E. In vivo effect of CBZ on (A) hepatic AT load, (B and C) globules, (D) autophagosomes, and (E) hepatic-fibrosisin PiZ×GFP-LC3 mice. Male mice at 5 months of age were treated for 2 weeks with CBZ (250 mg kg-1) or solvent (dimethyl sulfoxide) by gavage. Samples from two control and two CBZ-treated mice are shown. (A) Immunoblot; (B) histochemical staining with periodic acid-Schiff and diastase; (C) immunostaining with anti-AT; (D) immunostaining with anti-GFP; (E) histochemical staining with Sirius red. Globules are purple in (B). Globules are red and nuclei blue in (C). Autophagosomes are green in (D). Scale bars, 100 mm.

Figure 5A:
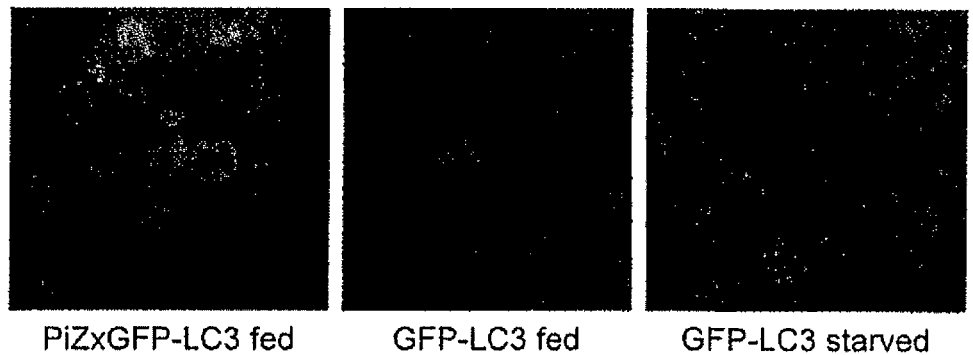
Figure 5B:
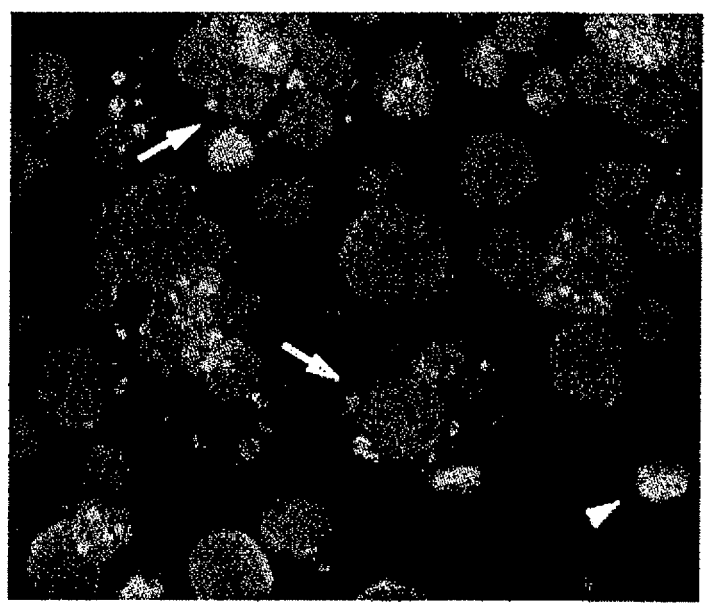
Figure 5C:
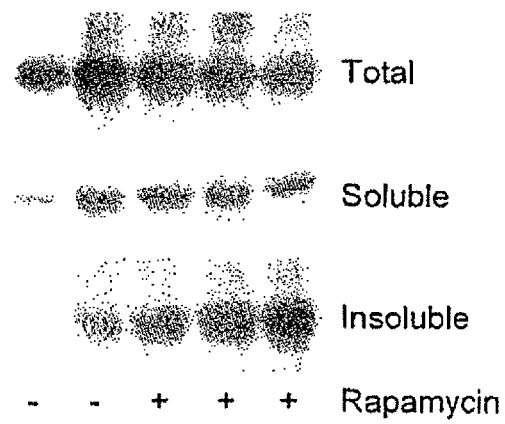

FIG. 5A-C. (A) Green fluorescent autophagosomes in the liver of PiZ×GFP-LC3 and GFP-LC3 mice. At 5 months of age, male mice were sacrificed after 24 hours of regular feeding or starvation. Liver sections were stained with anti-GFP to enhance the detection of green fluorescent autophagosomes. The results indicate that hepatic autophagy is activated in the PiZ mouse without stimulation by starvation whereas hepatic autophagy is only activated in the GFP-LC3 mouse after starvation. (B) Relationship between green fluorescent autophagosomes and ATZ-containing globules in liver cells of untreated PiZ×GFP-LC3 mice. Liver from 5-month old males was doublestained with anti-AT (with secondary antibody for red fluorescence) and anti-GFP. The arrows point to globule-containing hepatocytes and the arrowhead points to a globule-devoid hepatocyte. The result demonstrate the autophagosomes are predominantly located in globule-containing hepatocytes in the liver of PiZ mice that have not been treated with CBZ. (C) Effect of rapamycin on hepatic AT accumulation in PiZ mice. Male PiZ mice at 5 months of age were treated for 2 weeks with rapamycin 2 mg/kg/day by intraperitoneal injection every other day. The control group received the solvent DMSO in the identical volume. Livers were harvested and AT levels determined by immunoblot as described above.

Figure 6:
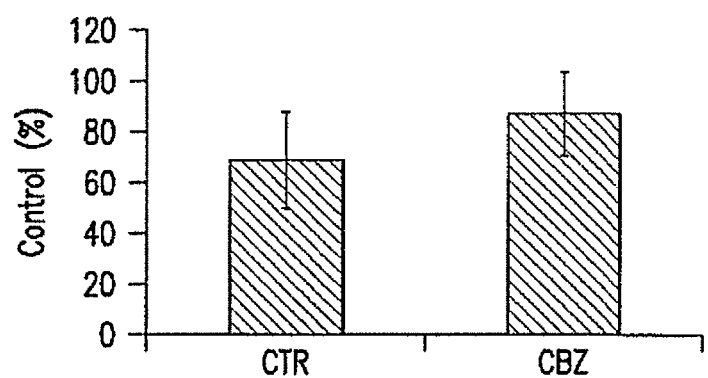

FIG. 6. Effect of CBZ on serum levels of human ATZ in PiZ mice. Serum levels were determined by ELISA specific for human AT. Sufficient amount of serum was available from 11 control PiZ mice and 18 PiZ mice treated with CBZ 250 mg/kg/day for 2 weeks. Results are shown as mean+/−SD.

Figures 7, 8:
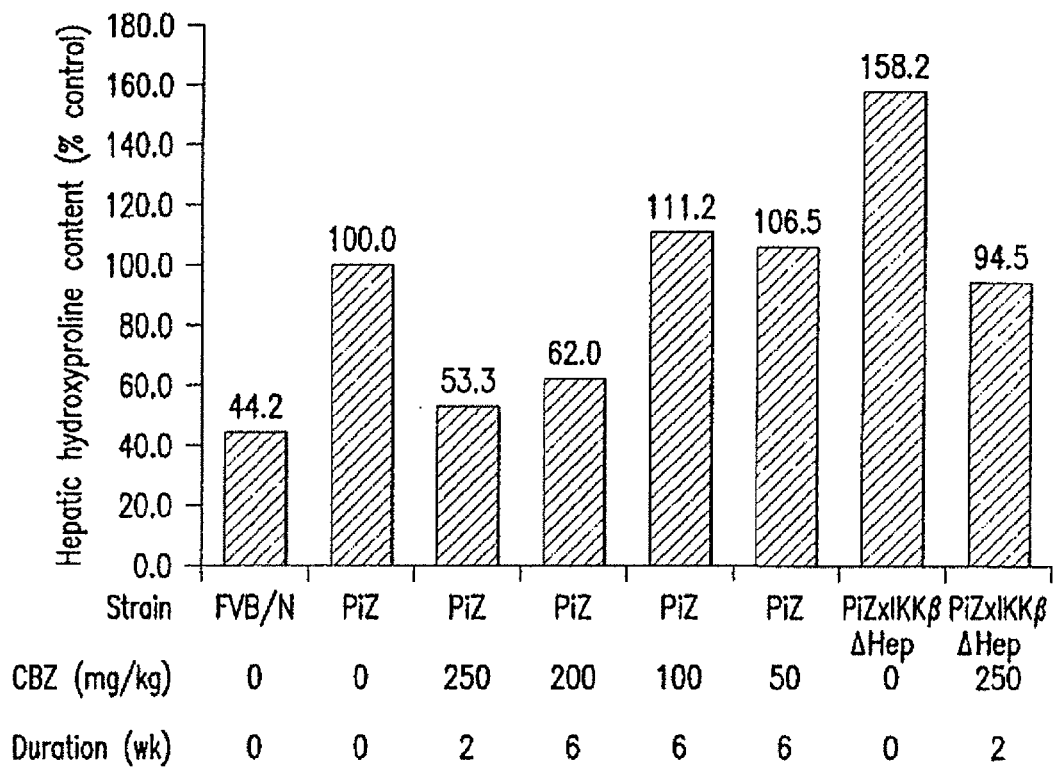

FIG. 7. Hepatic hydroxyproline content in FVB/N, PiZ and PiZ×IKKβ.hep mice in the absence or presence of CBZ treatment. The results are shown as % control with the hepatic hydroxyproline content in the untreated PiZ mouse set at 100%. Mouse strain, dose of CBZ and duration of CBZ treatment are shown at the bottom. The absolute figure for % control is shown at the top of each bar.

FIG. 8. Levels of smooth muscle actin, collagen IA and TGFβ RNA reported as mean+/−SD. As determined by Q-PCR.

Figure 9:
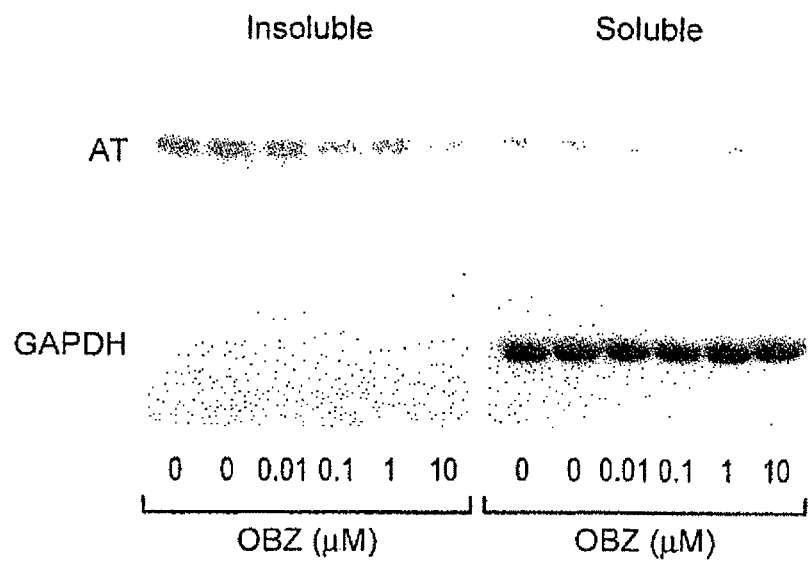

FIG. 9. HTO/Z cells were incubated for 48 hrs in the absence or presence of OBZ. Insoluble and soluble fractions from cell homogenates were subjected to western blot for ATZ and GAPDH.

Figure 10:
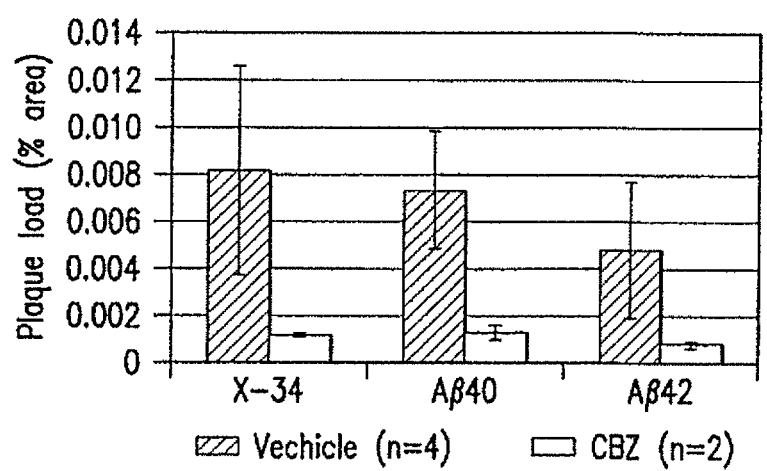

FIG. 10. Plaque load detected by staining of brain sections with x-34, anti-Aβ1-40 or anti-Aβ1-42.

Figure 11:
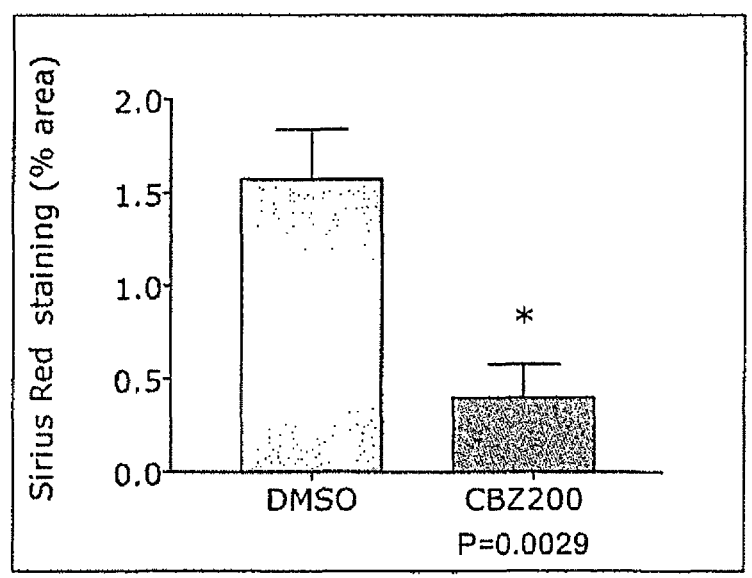

FIG. 11. Effect of CBZ on pulmonary fibrosis in PiZ× GFP-LC3 mice. Sirius Red staining (% area) was measured. 3 month-old mice were treated for 3 weeks, 5 days per week, by oral gavage. Doses are mg/kg/day. * denotes significant difference from the DMSO control.

5. DETAILED DESCRIPTION OF THE INVENTION

For clarity of description and not by way of limitation, the detailed description of the invention is divided into the following subsections:
(i) treatment agents;
(ii) disorders of protein polymerization; and
(iii) methods of treatment.

5.1 Treatment Agents

Treatment agents which may be used according to the invention include carbamazepine ("CBZ"), oxcarbazepine ("OBZ") and other CBZ-like compounds.

CBZ is 5H-dibenz [b,f]azepine-5-carboxamide. The chemical structure of CBZ is shown in Formula I:

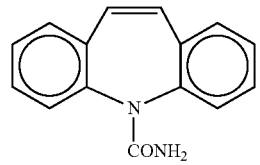

Oxcarbazepine, also known by the trade name Trileptal® is 10,11-dihydro-10-oxo-5H-dibenz[b,f]azepine-5-carboxamide, and its structural formula is:

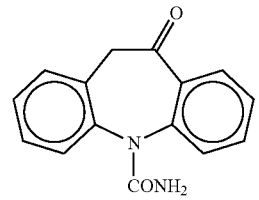

Other CBZ-like compounds include CBZ metabolites, including but not limited to carbamazepine-10,11-epoxide and iminostilbene, as well as structurally related compounds, and oxcarbazepine metabolites, such as but not limited to 10,11-dihydro-10-hydroxy-carbamazepine (also known as "MHD"). Non-limiting examples of compounds structurally related to CBZ and OBZ include dihydro-CBZ, ethyl urea, phenyl urea, diphenylurea, dicyclohexylurea, phenytoin, substituted and unsubstituted iminobenzyl compounds, imipramine, (S)-(−)-10-acetoxy-10,11-dihydro-5H-dibenz[b,f]azepine-5-carboxamide (BIA 2-093), and 10,11-dihydro-10-hydroxyimino-5H-dibenz[b,f]azepine-5-carboxamide (BIA 2-024) (22, 23, 24). CBZ and CBZ-like compounds that are able to cross the blood brain barrier offer advantages for the treatment of disorders of protein polymerization in the central nervous system. The ability of compounds structurally related to CBZ to treat disorders of protein polymerization may be confirmed to have activity in decreasing protein polymers (aggregates), for example, using the HTO/Z cell line or its equivalent, or the PiZ×GFP-LC3 transgenic mouse or its equivalent, or the model system developed in *Caenorhabditis elegans*, as described in U.S. Provisional Application No. 61/258,384, filed Nov. 5, 2009.

5.2 Disorders of Protein Polymerization

Disorders of protein polymerization (also sometimes referred to in the art as disorders of protein aggregation or accumulation) that may be treated according to the invention include, but are not limited to, α1-antitrypsin deficiency, hepatic fibrosis, pulmonary fibrosis, Alzheimer's Disease, Parkinson's Disease, Pick's Disease, corticobasal atrophy, multiple system atrophy, Lewy Body Disease, familial encephalopathy with neuroserpin inclusion bodies (FENIB), Huntington's Disease, amyloidosis (e.g., primary, secondary, familial, senile), prion-associated diseases (e.g., Creuzfeld-Jacob disease, mad cow's disease), protein polymerization resulting from ischemic or traumatic brain injury (for example dementia pugilistica (chronic traumatic encephalopathy)), progressive supranuclear palsy, Lytico-Bodig disease (Parkinson dementia complex of Guam), ganglioma, subacute sclerosing panencephalitis, certain forms of congenital diabetes, certain forms of retinitis pigmentosa, certain forms of long QT syndrome, hereditary hypofibrinogenemia, certain forms of osteogenesis imperfecta, certain forms of hereditary angioedema, Charcot-Marie-Tooth disease and Pelizaeus-Merzbacher leukodystrophy.

5.3 Methods of Treatment

The present invention relates to methods of treating clinical disorders associated with protein polymerization comprising administering, to a subject in need of such treatment, an effective amount of CBZ or a CBZ-like compound.

A subject in need of such treatment may be a human or a non-human subject, and may be suffering from a disorder associated with protein polymerization or be at risk of developing such a disorder due to age, family history, or exposure to a toxic agent.

An effective amount, as that term is used herein, is an amount that (i) reduces one or more sign and/or symptom of the disorder; and/or (ii) inhibits progression of the disorder; and/or (iii) prolongs survival of the subject. It is this reduction in a sign and/or symptom, inhibition of progression, or prolongation of survival which constitutes treatment of the disorder.

Signs and symptoms of a disorder associated with protein polymerization depend upon the particular disorder and are known to the person skilled in the art. For all disorders treated according to the invention, one sign that may be "reduced" may be the accumulation of polymerized protein, in which either the rate of accumulation may be slowed or (but not necessarily) the amount of polymerized protein accumulated may stabilize or decrease.

For example, but not by way of limitation, where the disorder is AT-deficiency, signs or symptoms that may be reduced or otherwise ameliorated according to the invention include hepatitis, hepatic enlargement, hepatic fibrosis, hepatocarcinoma, impaired liver function, abdominal distension from ascites, jaundice, edema, enlarged spleen, hypersplenism, gastrointestinal bleeding, encephalopathy, renal failure, prolonged bleeding from injuries, shortness of breath, wheezing, cough, decreased serum oxygen, increased serum carbon dioxide, increased total lung capacity, decreased FEV1/FVC ratio, increased incidence of pulmonary infection, pulmonary infection, weight loss and fatigue. Although the working example below addresses effects of ATZ accumulation on the liver additional evidence is consistent with a similar toxic function of ATZ in the lung, such that signs or symptoms of pulmonary dysfunction may be treated according to the invention.

As a further non-limiting example, where the disorder is Alzheimers Disease, signs or symptoms that may be reduced or otherwise ameliorated according to the invention include impairment of short term memory, impairment of abstract thinking, impairment of judgment, impairment of language skills, and mood changes.

As a further non-limiting example, where the disorder is Parkinson's Disease, signs or symptoms that may be reduced or otherwise ameliorated according to the invention include tremor, bradykinesia, rigidity, impaired speech, and dementia.

As a further non-limiting example, where the disorder is Huntington's Disease, signs or symptoms that may be reduced or otherwise ameliorated according to the invention include dementia and choreoform movements.

As a further non-limiting example, where the disorder is amyloidosis, signs or symptoms that may be reduced or otherwise ameliorated according to the invention include thickening of the skin, rash, cardiomyopathy, congestive heart failure, cardiac arrhythmias and/or conduction defects, shortness of breath, fatigue, impaired renal function, hyothyroidism, anemia, bone damage/fracture, impaired liver function, impaired immunity, and glossitis.

As a further non-limiting example, where the disorder is a prion disease, signs or symptoms that may be reduced or otherwise ameliorated include dementia and choreoform movements.

In additional non-limiting embodiment, the present invention provides for a method of decreasing the amount of polymerized protein in a cell comprising exposing the cell to an effective amount of CBZ or a CBZ-related compound. The cell may be a cell affected by a disorder of protein polymerization, as set forth above, for example, but not by way of limitation, a liver cell or a lung cell from a subject suffering from AT deficiency, a neuron from a subject suffering from Alzheimer's Disease, Parkinson's Disease, Huntington's disease, a prion disease, or a cell from a subject suffering from any of the other aforelisted disorders associated with protein polymerization.

CBZ or a CBZ-related compound may be administered by any route of administration, including oral, intravenous, intramuscular, subcutaneous, intrathecal, intraperitorneal, intrahepatic, by inhalation, e.g., pulmonary inhalation, etc. In a preferred non-limiting embodiment of the invention, CBZ or a CBZ-related compound may be administered orally.

In preferred non-limiting embodiments of the invention, CBZ may be administered at a dose of 400 mg/day in 2-4 divided doses. Said dose may optionally be increased weekly by 200 mg until a therapeutically effective dose, or a dose of up to 1000 mg/day (for children 12-15 years of age) or a dose of up to 1200 mg/day (for persons greater than 15 years of age), is reached. Children between the ages of 6-12 may desirably be treated with an initial dose of 200 mg/day which is then increased weekly by 100 mg/day until a dose of 800 mg/day is reached. Children under 6 years of age may desirably be treated with CBZ at a dose of 10 mg/kg/day, which dose may be increased weekly by 5 mg/kg/day until a dose of 20 mg/kg/day is reached.

In certain non-limiting embodiments of the invention, the dose of CBZ administered produces a serum concentration or cerebrospinal fluid concentration of at least about 0.1 micromolar and preferably at least about 3 micromolar or at least about 1 microgram per milliliter. To determine the lower dosage limit of a CBZ-related compound, said related compound may be tested in an assay system as described in the example section below and the concentration of related compound which creates approximately the same inhibitory effect on ATZ accumulation as 3 mM CBZ may be determined.

In certain non-limiting embodiments of the invention, CBZ may be administered at a total dose of at least about 100 mg/day, which may optionally be administered as a divided dose.

In certain non-limiting embodiments of the invention, CBZ may be administered at a total dose of between about 25 and 1500 mg/day, or between about 100 and 1200 mg/day, or between about 400 and 1200 mg/day, or between about 100 and less than about 400 mg/day, any of which doses may optionally be administered as a divided dose.

Where a CBZ-like compound is used, the dose of compound may be determined based on the above doses for CBZ and a comparison of the related compound's potency to that of CBZ in reducing AZT accumulation in vitro or in vivo, for example as determined using one or more assay described in the example below.

For example, and not by limitation, the present invention provides for a method of treating clinical disorders associated with protein polymerization comprising administering, to a subject in need of such treatment, an effective amount of OBZ.

In certain non-limiting embodiments of the invention, OBZ may be administered at a total dose of between about 5 and 1500 mg/day, or between about 50 and 1000 mg/day, or between about 50 and 600 mg/day, or between about 50 and 300 mg/day, or between about 50 and 200 mg/day, or between 50 and less than about 300 mg/day, any of which doses may optionally be administered as a divided dose.

In certain non-limiting embodiments of the invention, the dose of OBZ administered produces a serum concentration or cerebrospinal fluid concentration of at least about 0.01 micromolar and preferably at least about 0.1 micromolar or at least about 1 microgram per milliliter.

In certain non-limiting embodiments of the invention, OBZ may be administered at a total dose of at least about 100 mg, which may optionally be administered as a divided dose.

In certain non-limiting embodiments, the dose may be administered daily, about every other day, about twice a week, or about once a week.

Treatment may be administered continuously or for intervals interrupted by breaks.

Prior to treatment with CBZ, it is desirable to test whether a subject carries the HLA-B* 1502 allele, as subjects carrying this allele may have a severe skin reaction to CBZ, which may include toxic epidermal necrolysis or Stevens Johnson Syndrome.

6. EXAMPLE

An Autophagy-Enhancing Drug Promotes Degradation of Mutant $\alpha_1$-Antitrypsin Z and Reduces Hepatic Fibrosis

6.1 Materials and Methods

Materials Rabbit anti-human AT antibody was purchased from DAKO (Santa Barbara, Calif.) and goat anti-human AT from Diasorin (Stillwater, Minn.). Antibody to GAPDH was purchased from US Biochemical and antibody to LC3 was from Axora LLC (San Diego, Calif.). Antibody to murine BiP was purchased from Santa Cruz Biotechnology (Santa Cruz, Calif.). Rapamycin (RAP) was purchased from Sigma and prepared as a stock solution of 2 mgs/ml in DMSO. Carbamazepine (CBZ) was purchased from Sigma and prepared in a stock solution of 25 mg/ml DMSO. Doxycycline was purchased from Sigma and prepared 1 mg/ml in water. MG132 was purchased from Calbiochem (stock solution 10 mM in DMSO), lactacystin from Boston Biochem (stock solution 10 mM in DMSO), E64D from Peptide International (stock solution 20 mg/ml in DMSO) and pepstatin A from Sigma (stock solution 20 mg/ml in DMSO).

Cell Lines The human epidermal HeLa cell line with doxycycline-regulated expression of ATZ (HTO/Z) has been described previously (1). HTO/M and HTO/Saar are HeLa cell lines with doxycycline-regulated expression of wild type AT and the AT Saar variant, respectively (1). A murine embryonic fibroblast cell line (MEF) with targeted disruption of Atg5 (2) was engineered for stable expression of ATZ using the previously described pRc/RSV-ATZ expression plasmid (3). A wild type MEF cell line was also engineered for stable expression of ATZ in the same way to serve as control. For experiments with CBZ, the inducible cell lines were cultured in the absence of doxycycline for at least 4 weeks for maximal expression of AT. The cells were then subcultured into separate monolayers in fresh complete growth medium and incubated for 48 hours in the absence or presence of CBZ or rapamycin (RAP). CBZ or RAP were added to the growth medium. The duration of incubation with CBZ was determined to be optimal at 48 hours based on experiments in which the duration was varied from 12 to 72 hours. Doses of CBZ were based on previous studies of its effects in cell lines (5,6). Doses of RAP were based on previous positive effects on autophagic disposal of polyglutamine-repeat proteins (7). After the incubation cells were homogenized and cell homogenates separated into insoluble and soluble fractions according to our previously established technique (8). Samples of 20 µgs each were subjected to immunoblot analysis for AT, BiP and GAPDH.

For experiments in which proteasomal inhibitors were used, MG132 was used at 30 µM and lactacystin at 10 µM for the last 6 hours of the incubation with CBZ or control. Cells that were incubated with MG132 or lactacystin alone served as control to validate that the proteasome was inhibited. For investigation of LC3 conversion, lysosomal inhibitors (E64D and pepstatin A at 20 µg/ml) were added to the medium for the last 4 hours of the incubation with CBZ or control. This has been shown to inhibit the lysosomal degradation of LC3-II and when compared to the LC3-II levels in the absence of lysosomal inhibitors to provide a true reflection of autophagic flux (9). If the number of separate experiments done in the cell line models is not specifically indicated in the text or figure legend, at least 3 separate experiments were done in each case.

Transgenic Mice PiZ mice that have been bred into the C57/BL6 background have been described previously (1). For the second and third series of experiments with CBZ we used PiZ mice that were re-derived onto the FVB/N background for a move into a new animal facility. The transgene that was used to generate the PiZ mouse is a genomic fragment of DNA that contains the coding regions of the ATZ gene together with introns and ~2 kilobases of upstream and downstream flanking regions (10). It is important to point out that the endogenous murine ortholog of AT is not knocked out in this mouse so it does not have deficient serum levels of AT. In this perspective it is not an exact phenocopy of the classical form of AT deficiency. In particular it cannot be a model for the loss-of-function mechanisms associated with the classical form of AT deficiency. It is known to have abundant expression of ATZ in hepatocytes and other cell types that express ATZ in humans (11). In the liver there are abundant ATZ-containing intrahepatocytic globules and inflammation that is characteristic of what is seen in the human liver (11,12). It was found that the liver of the PiZ mouse resembles that in humans with the classical form of AT deficiency in terms of regenerative activity, steatosis, dysplasia, mitochondrial injury, activation of autophagy, NFκB and genes associated with fibrosis (1, 12-16). In this study Sirius Red staining and quantification of hydroxyproline in the liver of these mice was used for the first time and it was found that there is also significant hepatic fibrosis, the most important hepatic histological marker of hepatic injury that occurs in the human disease. FIG. 7 shows that the hepatic hydroxyproline content is more than 2-fold higher than that in the background FVB/N strain. Taken together, these observations indicate that the PiZ mouse is an appropriate model for the gain-of-toxic function mechanism that is responsible for liver damage in the classical form of AT deficiency. Indeed, the fact that these mice are endowed with endogenous AT function and therein normal levels of AT in the serum and body fluids make them an even more 'pure' model for liver damage by gain-of-toxic function. PiZ×GFP-LC3 mice, which generated green fluorescent autophagosomes, have been described previously (2). PiZ×IKKβ.hep were generated by mating of PiZ to IKKβ.hep, which has conditional hepatocyte-specific disruption of NF.B activation (M. Karin, 17). There is increased injury in the liver of these mice as evidenced by the hepatic hydroxyproline content, 153.3% of that in the PiZ mouse (FIG. 7).

Histology Sections of liver tissue were stained with hematoxylin and eosin, PAS, PAS after diastase treatment, TUNEL, PCNA, Ki67 and Sirius Red using standard techniques (18). Previous methods for staining with antibody to smooth muscle actin were used (19). Each was examined by the pathologist (GM) who was completely blinded to the experimental protocol. Sections of liver tissue were also stained with goat anti-human AT followed by donkey anti-goat Cy3 to detect AT-containing intracellular globules. Finally sections of liver tissue were stained with anti-GFP to optimize the detection of green fluorescent autophagosomes. The number of inflammatory nodules, AT-containing globules and autophagosomes were each quantified blindly by counting cells in 6 microscopic fields of 10 different sections for each liver. The number of nuclei, as determined by Hoechst staining, was used to exclude the possibility that different numbers of cells were counted in liver sections from mice treated with CBZ as compared to controls. Hepatic hydroxyproline concentration was determined by a well-established protocol (20,21).

Therapeutic regimens For the initial series of experiments in mice in vivo, the dose of 250 mg/kg/day for CBZ was based on previous studies of its biological effects in mice (22,23). The duration of 2 weeks was more effective in reducing the hepatic ATZ load than 7 days or 10 days. CBZ was administered in DMSO by gavage once per day. Control mice were given an equivalent volume of DMSO by gavage. In a second series of experiments, doses of 200, 100 and 50 mg/kg/day of CBZ were administered for 6 weeks. The dose and route of administration of RAP, 2 mg/kg/day by intraperitoneal injection for 2 weeks, was based on previous studies that have shown activation of hepatic autophagy (24).

Quantitative PCR (Q-PCR) Levels of mRNA from smooth muscle actin, collagen IA and TGFβ in liver of PiZ mice were determined by Q-PCR using primers from ABI and previous described conditions (19).

Radioimmunoprecipitation, SDS-PAGE and Immunoblot Analysis Biosynthetic labeling, pulse-chase labeling, immunoprecipitation and SDS-PAGE/fluorography for AT followed previously published protocols (1). Radioactivity measured in TCA precipitates, using previous methods (1), did not show any effects of CBZ on total protein synthesis or secretion. For the pulse labeling experiments, HTO/Z cells were incubated for 48 hours in the absence or presence of CBZ in several different concentrations and then subjected to labeling for 30 mins. The cell lysates were then examined by immunoprecipitation and the immunoprecipitates analyzed by SDS-PAGE/fluorography. For the pulse-chase experiments, HTO/Z cells were incubated for 48 hours in the absence of presence of CBZ 30 µM and then pulse labeled for 30 mins. The cells were then washed and incubated in growth medium without tracer for several different time intervals to constitute the chase. CBZ 30 µM was included during the pulse and chase periods. The extracellular fluid and cell lysate samples were subjected to immunoprecipitation and the immunoprecipitates analyzed by SDS-PAGE/fluorography. All fluorograms were subjected to densitometry. The relative densitometric value of T0 is set at 100% and the remainder of the data set expressed as % of this control. The data are shown as mean+/−SE and the mean value at each time point is shown at the bottom of the figure.

For immunoblot analysis to detect AT, GAPDH or LC3, cells were lysed in 50 mM Tris-HCl, 150 mM NaCl, 1% NP-40, pH 8.0. Protein levels were quantified using the BCA protein assay (Pierce Biotechnology, Rockford, Ill.). 10-50 µg samples were loaded onto 7.5% precast gels. PVDF membranes were blocked in TBS, 0.5% Tween 20 (TBST), 5% milk and then incubated with primary antibody in 5% milk TBST solution. Horseradish peroxidase anti-goat Ig or anti-mouse Ig (Jackson Labs, Bar Harbor, Me.) were used as secondary antibodies in TBST. Blots were visualized with Super Signal West Dura or West Femto from Pierce.

For immunoblot on liver, the liver was snap frozen in liquid nitrogen and stored at −80° C. Liver was homogenized in 50 mM Tris-HCl pH 8.0, 150 mM NaCl, 2 mM KCl, 2 mM MgCl2, 0.5% Triton X-100, 0.5% deoxycholic acid containing 0.1 mM phenylmethylsulfonic acid and complete protease inhibitor cocktail from Roche. Total protein concentration was measured by BCA assay (Pierce). Soluble and insoluble fractions were separated by centrifugation (14,000 rpm, 10 min, 4° C.). The insoluble pellet was washed twice in 50 mM Tris-HCl (017.4, 150 mM NaCl) and resuspended in 50 mM Tris-HCl (pH6.8, 5% SDS, 10% glycerol). Equal amounts of total protein (1 ug) were loaded on 8% SDS-PAGE. After transfer to PVDF membrane, the blots were blocked in PBS-Tween20 containing 5% non-fat milk for 1 hr at RT, then goat-anti human AT antiserum (Diasorin, 1:2500) was applied followed by three washes. Donkey anti-goat IgG-HRP (Santa Cruz, 1:1,000,000) and West Dura (Pierce) was used for detection of AT. The blots were stripped (Pierce) and after the blocking step anti-mouse GAPDH (US Biologicals, 1:10,000) and rabbit anti-mouse IgG-HRP (Jackson Labs, 1:5000) were used to detect GAPDH.

For ELISA on mouse serum specimens, Nunc Maxisorp plates were first coated with goat anti-human AT (Bethyl), then blocked in PBS-Tween20 containing 5% nonfat milk. Serum samples were loaded into the wells in 1:20,000 dilution using purified human AT serial dilutions (1.56 to 100 ng/ml) as a standard. Rabbit-anti human AT (Dako) was used as capturing antibody, and goat anti-rabbit IgG-HRP (Dako) a secondary antibody. Protein levels were detected with OPD (Sigma).

Statistical analysis Students t-test was used for most comparisons but the Welch-modified t-test was used to compare experimental groups that were not paired and did not assume equal variances. Kinetic curves were analyzed by two-way ANOVA with the Bonferroni post-test using the Prism software application.

6.2 Results and Discussion

The classical form of α1-antitrypsin (AT) deficiency is caused by a point mutation (lysine for glutamate 342) that alters the folding of an abundant liver-derived plasma glycoprotein during biogenesis and also renders it prone to polymerization (25). In addition to the formation of insoluble aggregates in the endoplasmic reticulum (ER) of liver cells, there is an 85-90% reduction in circulating levels of AT, the pre-dominant physiologic inhibitor of neutrophil elastase. Liver fibrosis and carcinogenesis are caused by a gain-of-toxic function mechanism. Indeed, AT deficiency is the most common genetic cause of liver disease in childhood but can also present for the first time with cirrhosis and/or hepatocellular carcinoma in adulthood (25).

Genetic and/or environmental modifiers determine whether an affected homozygote is susceptible to liver disease (26). Two general explanations for the effects of such modifiers have been postulated: variation in the function of intracellular degradative mechanisms (27,28) and/or variation in the signal transduction pathways that are activated to protect the cell from protein mislocalization and/or aggregation. As for degradation, the proteasome is responsible for degrading soluble forms of α1-antitrypsin Z (ATZ) (29), and macro-autophagy is specialized for disposal of the insoluble polymers and aggregates (30, 31). However, disposal of ATZ may involve other degradative mechanisms, as yet not well defined (32, 1). In terms of cellular response pathways, accumulation of ATZ activates nuclear factor kB(NF-kB) and autophagy but not the unfolded protein response (30, 1, 16).

Because the autophagic response participates in both degradation of ATZ and in the cellular response to accumulation of ATZ in the ER, we examined whether a drug that enhances autophagy could ameliorate hepatotoxicity in this disorder. From a list of drugs that have been recently shown to enhance autophagic degradation of aggregation-prone proteins with polyglutamine repeats (5, 33, 34), we selected carbamazepine (CBZ) for detailed studies of its effect on ATZ because it has the most extensive safety profile in humans.

Figure 1B:
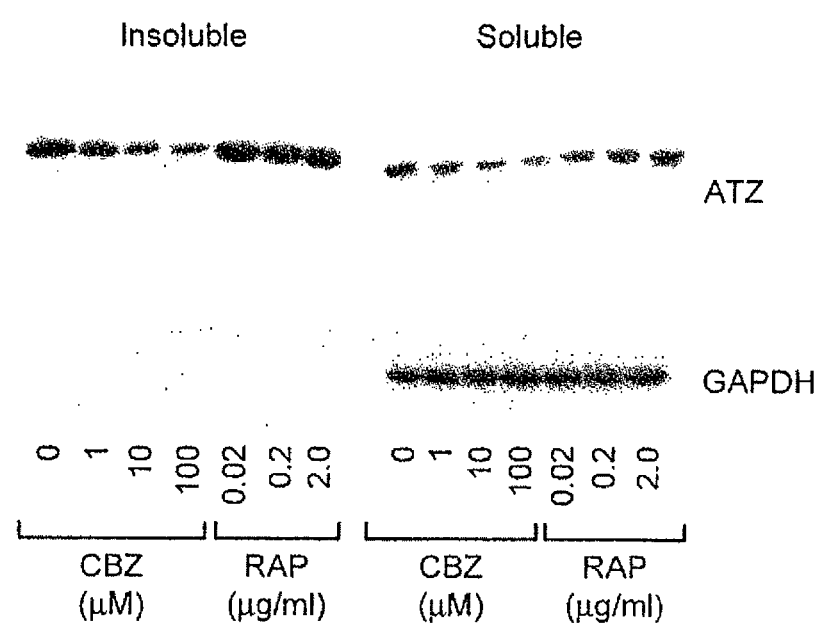
Figure 1C:
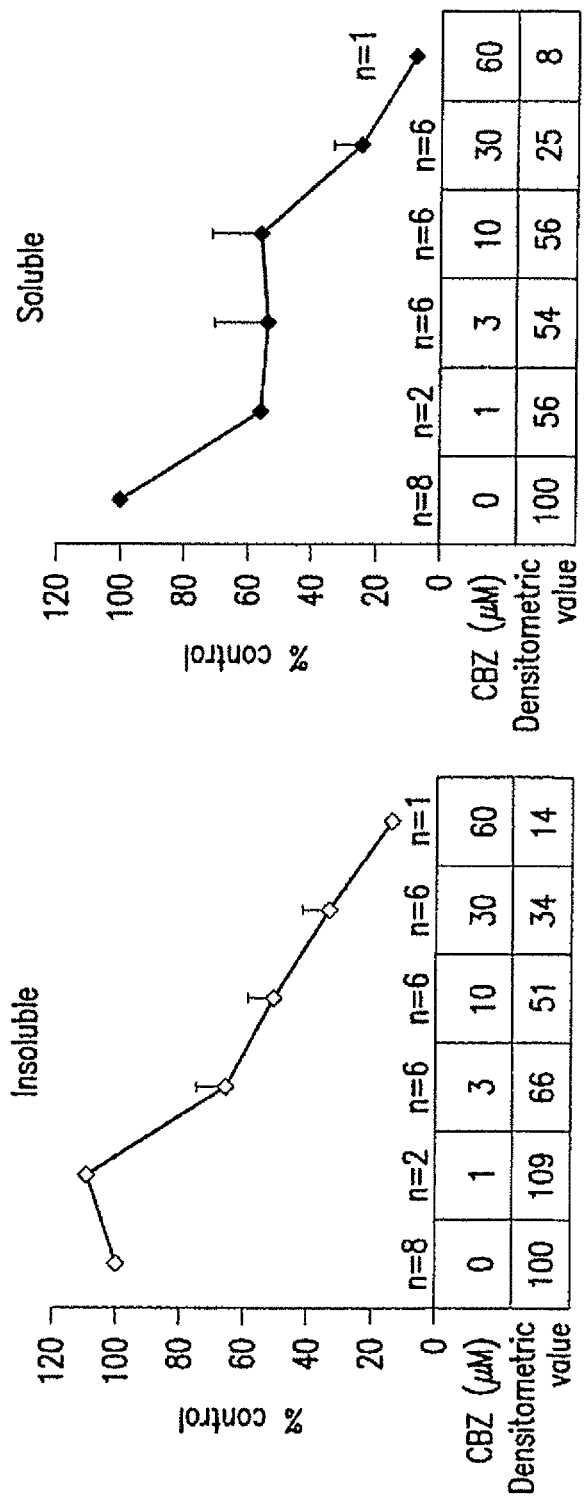
Figure 1D:
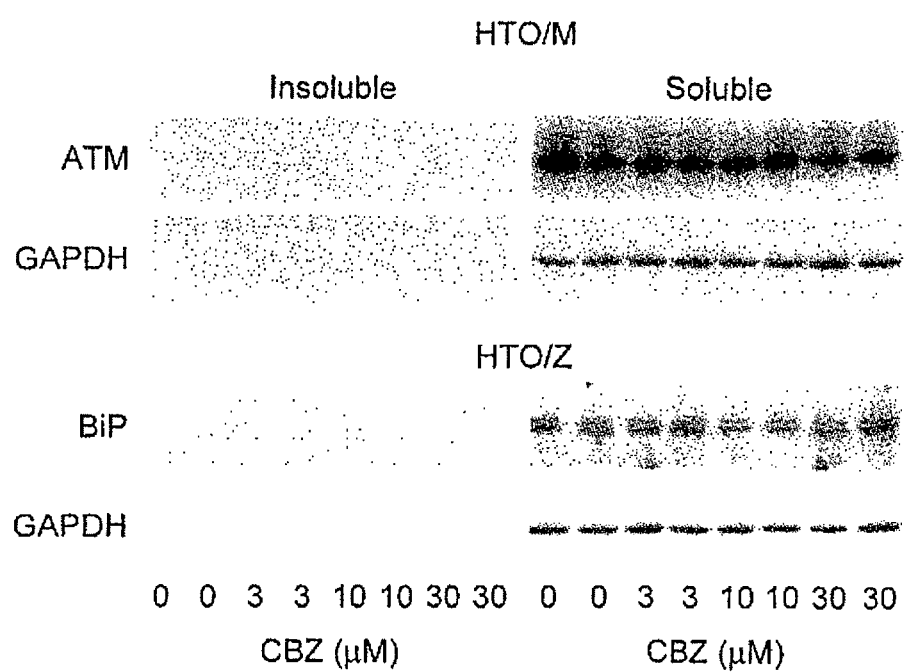

First, we found that CBZ mediated a marked decrease in steady-state levels of ATZ in both the insoluble and soluble fractions in the HeLa inducible cell line HTO/Z (FIG. 1A). The effect of CBZ was also specific because rapamycin, a drug that activates autophagy by inhibiting target of rapamycin (TOR) kinase, had no effect on ATZ levels (FIG. 1B). CBZ was dose dependent in the range of 1 to 60 mM (FIG. 1C) and did not affect wild-type AT levels in the HTO/M cell line or BiP levels in the HTO/Z line (FIG. 1D).

Figure 2A:
Figure 2B:
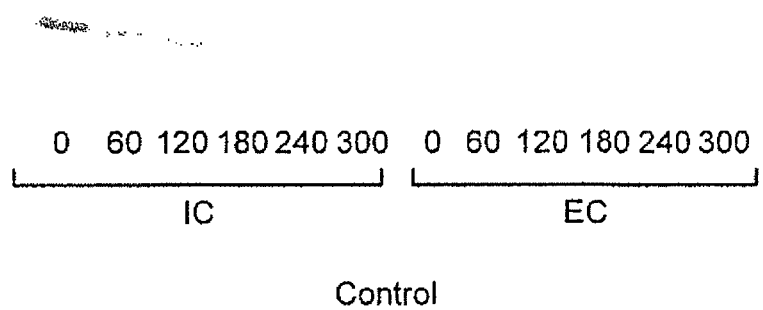
Figure 2C:
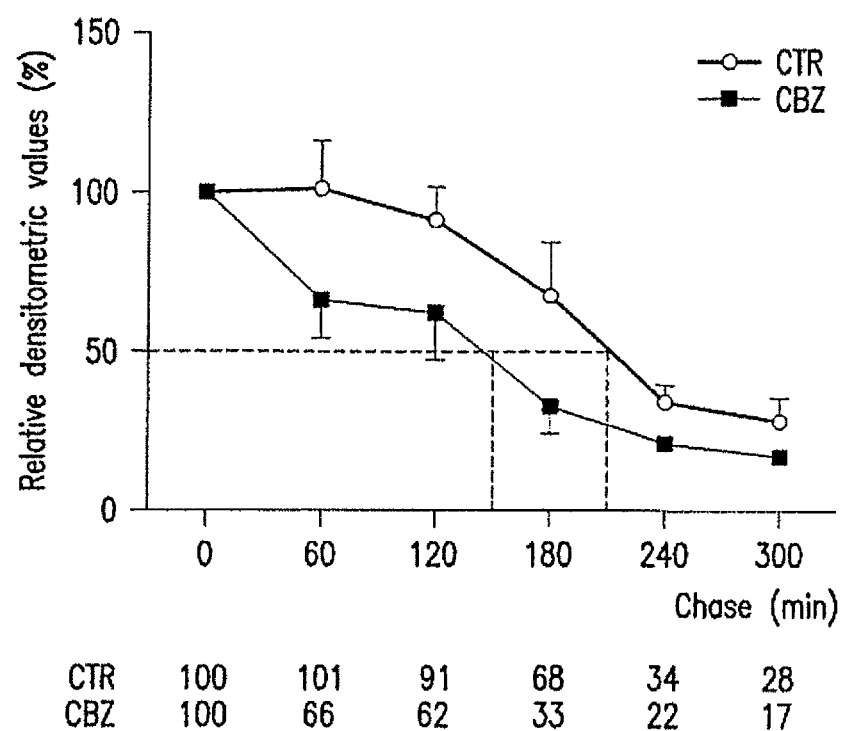
Figure 2D:
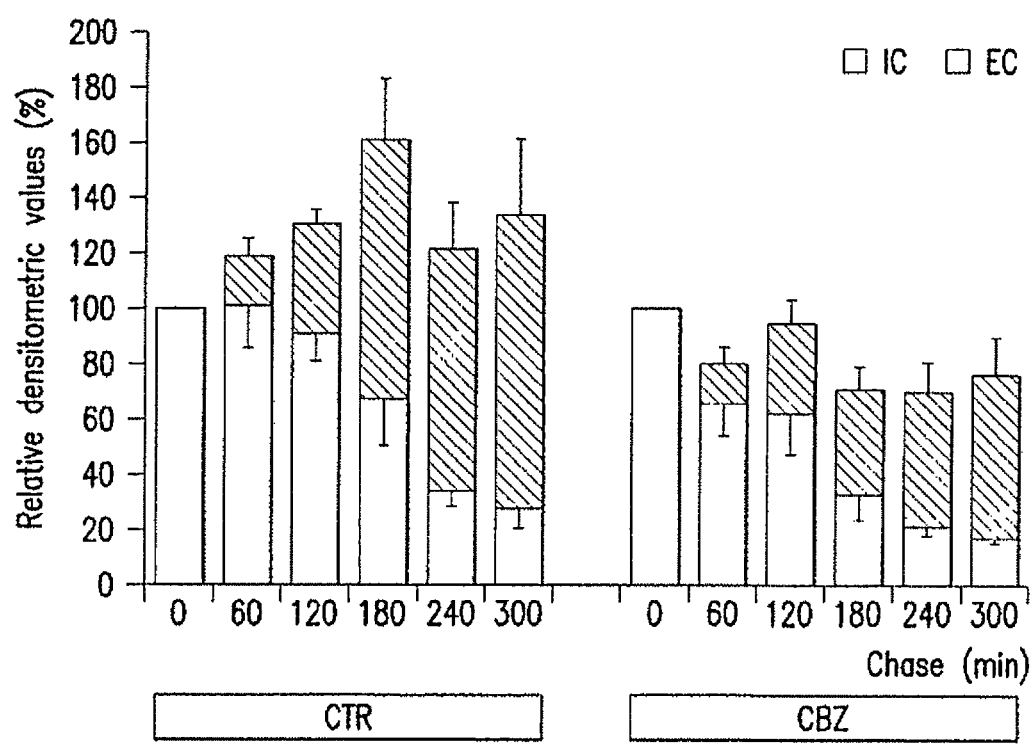

To further characterize the effect of CBZ on ATZ, we carried out pulse labeling and pulse-chase labeling experiments in the HTO/Z line. CBZ did not affect synthesis of ATZ (FIG. 2A), and disappearance of ATZ from the intracellular compartment was more rapid in cells treated with CBZ than in the untreated cells (FIG. 2, B and C). A statistically significant increase in disappearance of ATZ from the intracellular compartment was mediated by CBZ (P=0.0007 by two-way analysis of variance with Bonferroni adjustment), with a half-time of 130 min compared to 200 min in untreated cells. The increase in intracellular disappearance of ATZ mediated by CBZ could not be attributed to enhanced secretion (FIGS. 2B and 2D). Thus, CBZ appears exclusively to change the rate of intracellular degradation.

Figure 3A:
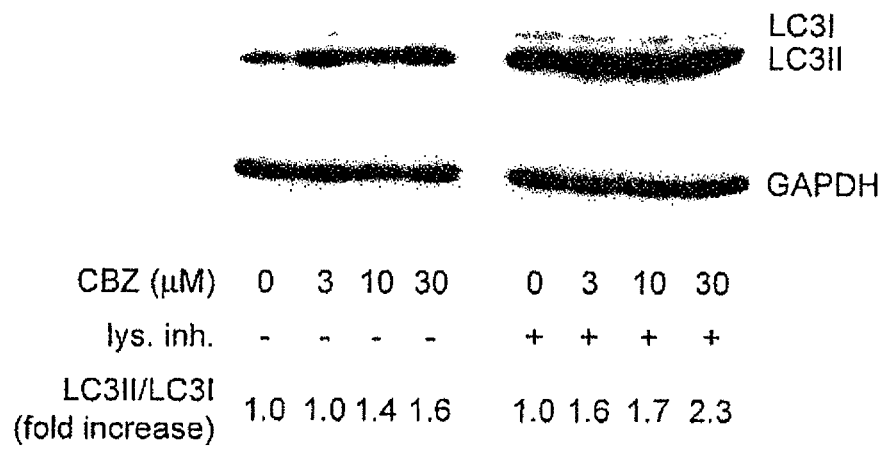

To determine whether CBZ enhances autophagy in the HTO/Z line, we examined its effect on isoform conversion of autophagosomal membrane-specific protein LC3, an indicator of autophagosome formation (FIG. 3A). The LC3-II to LC3-I ratio increased in a dose-dependent manner and was greater in the presence of lysosomal enzyme inhibitors, indicating that CBZ elicits increased autophagic flux. This effect of CBZ on autophagic flux exceeded the increase that results from intracellular accumulation of ATZ (FIG. 3F).

Thus, CBZ stimulates autophagy in cells that have already activated the autophagic pathway in response to ER accumulation of ATZ.

Figure 3B:
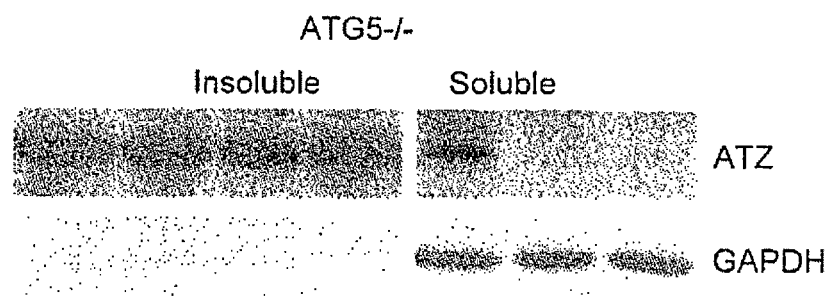
Figure 3C:
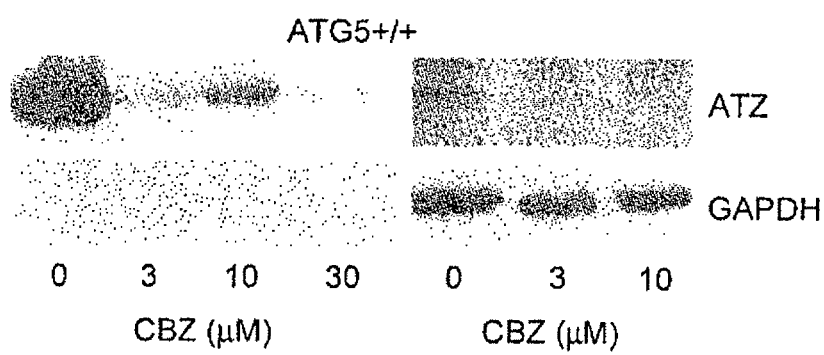
Figure 3D:
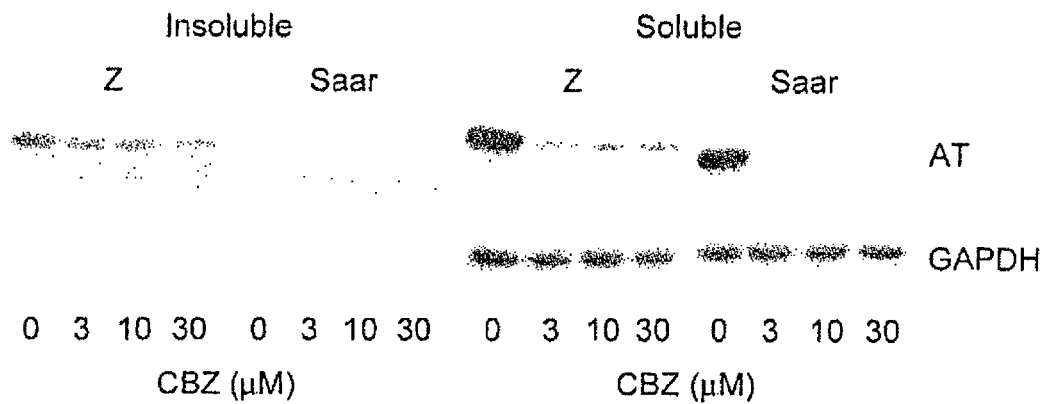

To determine whether the effect of CBZ on ATZ degradation involved enhanced autophagy, we examined its effect on ATZ levels in an autophagy (Atg5)-deficient cell line (FIGS. 3B and 3C). CBZ mediated a decrease in levels of insoluble ATZ in the wild-type mouse embryonic fibroblast (MEF) cell line but not in the Atg5 deficient cell line. CBZ also mediated a decrease in levels of soluble ATZ in both wild-type and Atg5-deficient cells. Thus, CBZ enhances the disposal of insoluble ATZ by autophagy and has an independent action on the disposal of soluble ATZ by mechanism(s) that do not involve the conventional autophagic pathway.

To determine whether the effects of CBZ were specific for the Z variant of AT, we investigated its effect on disposal of AT Saar, a variant of AT that accumulates in the ER but does not aggregate and is predominantly degraded by a proteasomal mechanism (1). AT Saar was present only in the soluble fraction, but it was degraded by CBZ in a manner almost identical to that of ATZ (FIG. 3D), suggesting an effect of CBZ also on the proteasome.

Figure 3E:
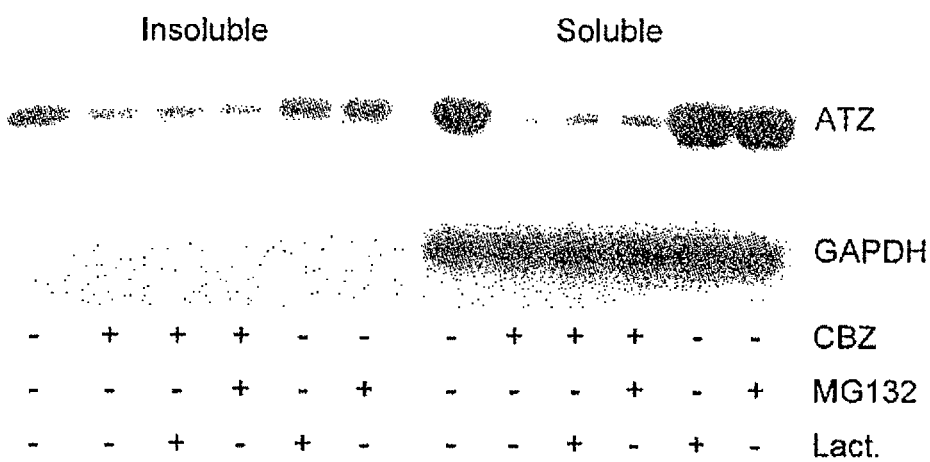
Figure 3F:
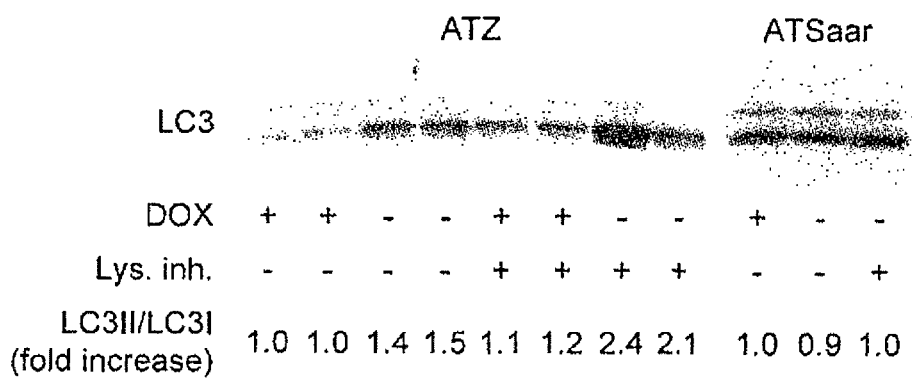

Thus, we examined the effect of CBZ on steady-state levels of ATZ in the presence of proteasomal inhibitors (FIG. 3E). Although they had no effect on levels of insoluble ATZ, lactacystin and MG132 partially reversed the effect of CBZ on levels of soluble ATZ [lactacystin: reversal of 23.1±14.0% (mean T SD), n=3 experiments; MG132: reversal of 12.3, average of n=two experiments]. Increased levels of ATZ in the presence of lactacystin and MG132 alone provided validation for proteasome inhibitory activity under the conditions of these experiments. Thus, CBZ mildly enhances proteasomal degradation of ATZ and has an independent action on nonproteasomal mechanisms for disposal of soluble ATZ.

Figure 4A:
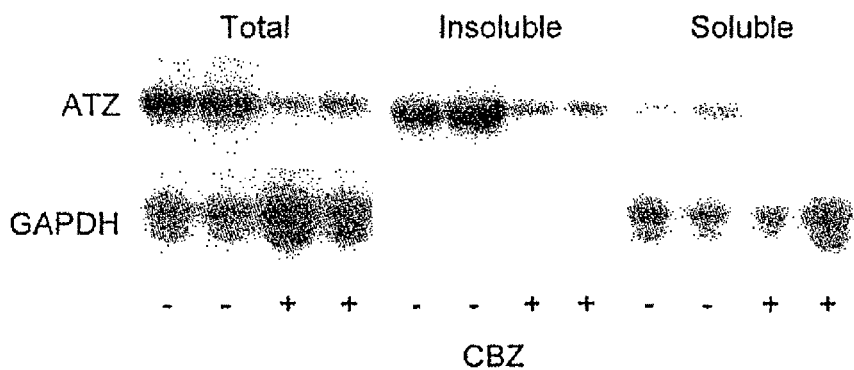
Figure 4B:
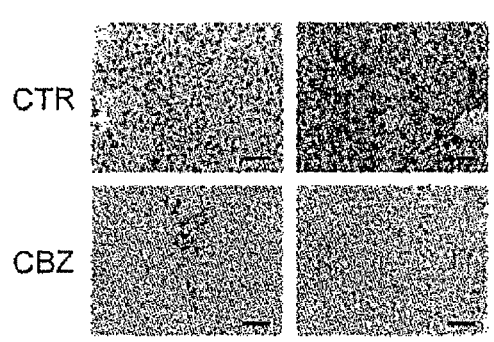
Figure 4D:
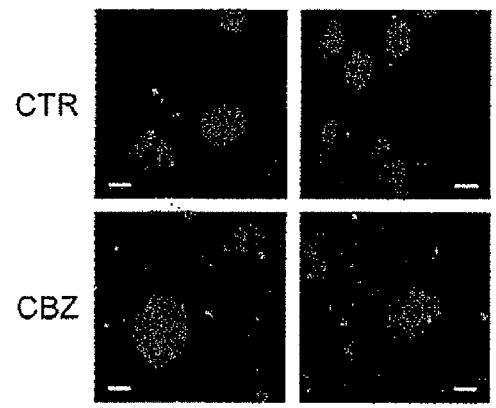
Figure 4C:
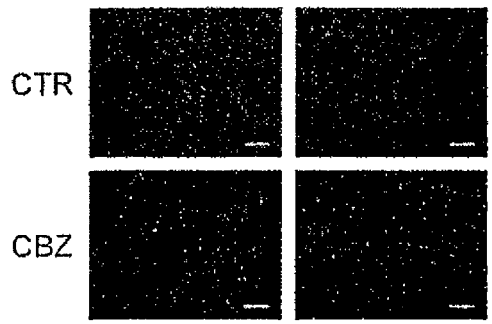

Next, we examined the effect of CBZ on hepatic load of ATZ in vivo using PiZ×GFP-LC3 mice. The PiZ mouse was created with the human ATZ gene as transgene. Although it differs from the human disorder in having normal circulating levels of the endogenous murine ortholog of AT, the PiZ mouse is a robust model of liver disease associated with AT deficiency, as characterized by intrahepatocytic ATZ-containing globules, inflammation, and increased regenerative activity, dysplasia, and fibrosis (12). It has been bred onto the GFP-LC3 background to monitor autophagy (30). When administered at 250 mg kg-1 day-1 for 2 weeks by gavage, CBZ mediated a marked decrease in total, insoluble, and soluble ATZ in the liver (FIG. 4A). The treatment was also associated with a marked decrease in intrahepatocytic ATZ-containing globules (FIGS. 4B and 4C). Quantitative morphometry showed a decrease in globule-containing hepatocytes by a factor of 3.36 (P<0.001 by Mann-Whitney rank sum test). Serum concentrations of human AT were not significantly affected by CBZ treatment (FIG. 6), arguing against any effect on secretion of ATZ in vivo.

Figure 4E:
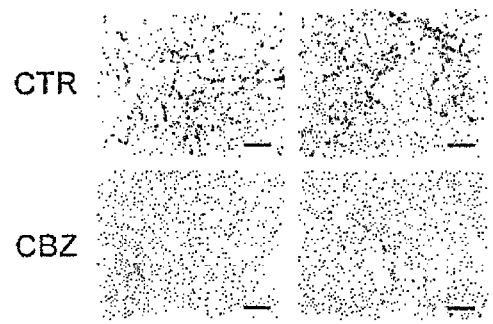

Using indirect immunofluorescence, an increase in number of hepatic green fluorescent autophagosomes was detected in areas of liver that lacked AT-stained globules after CBZ treatment (FIG. 4D), and this was confirmed by quantitative morphometry (mean±SD: 565.7±185.7 mm2 in control versus 1055.3±139.7 mm2 in CBZ; P=0.049 by t test). The increase in autophagosomes mediated by CBZ superseded the increase that occurs predominantly in globule-containing hepatocytes from ATZ expression alone (30) (FIGS. 5A and 5B). The effect of CBZ in vivo was specific in that rapamycin had no effect on hepatic ATZ levels (FIG. 5C). Next, we examined the effect of CBZ on hepatic fibrosis because it is a key feature of the liver disease associated with AT deficiency (12). CBZ mediated a marked decrease in fibrosis (FIG. 4E). Furthermore, there was a marked and statistically significant reduction in hepatic hydroxyproline concentration in PiZ mice treated with CBZ (mean±SD: 1.21±0.7 in CBZ versus 2.27±1.02 mg per milligram of dry weight in control, P=0.0074 by t test with Welch modification). Hepatic hydroxyproline content was decreased 46.7% by CBZ, reaching a level that was indistinguishable from that of the background FVB/N strain (FIG. 7). CBZ also mediated a decrease in hepatic hydroxyproline concentration in the PiZxIKKbDhep mouse model (FIG. 7). On this hepatocyte-specific NFkB-deficient background, there is more severe liver damage as reflected by hydroxyproline concentrations that are >150% of the levels in the PiZ mouse on the FVB/N background (FIG. 7). CBZ treatment decreased levels of stellate cell activation markers, including smooth muscle actin, collagen 1A, and transforming growth factor b, but only the decrease in actin reached statistical significance (FIG. 8).

To determine whether lower doses of CBZ for more prolonged time intervals could reduce hepatic fibrosis, we examined the effect of CBZ at lower doses for 6 weeks. Hepatic hydroxyproline concentrations decreased at the dose of 200 mg kg-1 day-1 but not at doses of 50 and 100 mg kg-1 day-1 (FIG. 7). Although the lowest effective dose of CBZ (200 mg kg-1 day-1) was considerably higher than the doses used in humans (10 to 20 mg kg-1 day-1), effective doses of drugs can be 10 to 20 times as high in mice because of the higher ratio of surface area to body weight when compared to humans.

Thus, CBZ reduces the hepatic load of mutant ATZ and hepatic fibrosis in the PiZ mouse. Mechanistic studies indicate that CBZ increases both autophagic and proteasomal degradation of ATZ. That rapamycin does not enhance autophagic disposal of ATZ may mean that a TOR-independent pathway is involved in the effect of CBZ. The effect of CBZ on ATZ disposal cannot be fully accounted for by the proteasomal and conventional macroautophagic pathways. The capacity to enhance disposal of both insoluble and soluble ATZ could represent an important characteristic of CBZ as a potential therapeutic in that it might provide for elimination of the putative hepatotoxic form of ATZ, whether it is soluble monomeric, soluble oligomeric, and/or insoluble polymeric ATZ species.

Because it is theorized that clinically significant liver damage occurs only in AT-deficient patients who also have a "second" defect in quality control and that these second defects are heterogeneous among the affected population, one might conclude that CBZ would be effective only in individuals in whom the "second" defect is related to the specific mechanism of CBZ action. However, our results suggest that CBZ can enhance autophagy beyond the extent to which it has already been activated by the pathological state. CBZ also appears to affect several mechanisms of intracellular disposal and therefore may not require mechanistic specificity for a beneficial effect. It is also encouraging that CBZ reduced hepatic fibrosis in the PiZxIKKbDhep mouse model, which could be viewed as a mouse with a type of "second" defect—in this case, reduced functioning of the hepatocyte NF-kB signaling pathway.

In addition to its potential for the treatment of liver disease due to AT deficiency, CBZ should be considered for its ability to enhance intracellular disposal pathways for the treatment of other diseases in which tissue damage involves gain-of-toxic function mechanisms caused by misfolded or aggregation-prone proteins (34). Our results also provide further evidence for the concept that the endogenous protein homeostasis machinery can be used to prevent tissue damage from mutant proteins (35).

7. EXAMPLE

Oxcarbazepine Decreases Cellular ATZ Load at Lower Doses than CBZ

OBZ is a structural derivative of CBZ and has been used extensively with an exceptional safety profile. Like CBZ it permeates the blood-brain barrier but it has several advantages over CBZ: it does not induce the liver microsomal membranes and cytochrome P450 activities; it does not cause the serious side effects of anemia and agranulocytosis that occasionally develop from CBZ administration. The effect of OBZ on steady state levels of ATZ in the HTO/Z cell line (FIG. 9) was evaluated. It was found that OBZ mediated a marked decrease in insoluble ATZ. The effect was dose-dependent with an effect evident at doses as low as 0.1 uM. This means that OBZ is effective at significantly lower doses than CBZ, which has a minimal effective dose of 3 μM. OBZ is also different than CBZ in that it appears to have a minimal effect on soluble ATZ levels, suggesting that it only stimulates autophagy.

8. EXAMPLE

CBZ Reduces Plaque Load in a Mouse Model of AD

The APP-PS1 mouse model of AD is associated with accelerated amyloid deposition with plaques resembling AD in humans starting to appear at 12 weeks of age (12) and progressive behavioral changes starting at 6 months of age (55, 56). Only a limited number of mice were available at the ideal age, 9 wks, at the time of the study, so the pilot study was very small. 9-12 wks of age was selected as the ideal age because it represents the age with the earliest consistent appearance of AP deposition in APP-PS1 mice. Mice were treated by orogastric gavage with CBZ 200 mg/kg/day, 5 doses per wk, for 3 wks; n=2 for CBZ and n=4 for vehicle (DMSO). Brain sections were stained with X-34, antibodies to Aβ1-40 and Aβ1-42 to determine plaque load using techniques as described previously (57). FIG. 10 shows that CBZ mediated a marked reduction in plaque load. ELISA for soluble and insoluble Aβ1-40 and Aβ1-42 using previously described methods (57) also showed a trend toward lower values in the CBZ-treated mice but with a much greater degree of variation.

9. EXAMPLE

CBZ Decreases Pulmonary Fibrosis in PiZ Mice

Experiments were performed to determine if CBZ can mediate a decrease in lung fibrosis in the PiZ mouse in vivo. 3-month-old PiZ mice were treated 5 days per week for 3 weeks with diluent DMSO or CBZ 200 mg/kg/day (n=3-8 mice per group). In this series of experiments lung fibrosis was assayed by Sirius Red staining with quantitative morphometry. The results, depicted in FIG. 11, show a statistically significant reduction in Sirius red staining (and hence pulmonary fibrosis) when PiZ mice were given CBZ. Of note, the drug treatment reduces lung fibrosis to levels that are comparable to what is found in wild type mice at this age.

10. REFERENCES

1. T. Hidvegi, B. Z. Schmidt, P. Hale, D. H. Perlmutter. J Biol Chem 280, 39002 (2005).
2. T. Kamimoto et al. J Biol Chem 281, 4469 (2006).
3. L. Lin, B. Schmidt, J. Teckman, D. H. Perlmutter. J Biol Chem 276, 33893 (2001).
4. N. Hosokawa, Y. Hara, N. Mizushima. FEBS Lett 580, 2623 (2006).
5. S. Sarkar et al. J Cell Biol 170, 1101 (2005).
6. J. Cui, L. Shao, L. T. Young, J.-F. Ward. Neuroscience 144, 1447 (2007).
7. Z. Berger et al. Hum Molec Genet 15, 433 (2006).
8. B. Z. Schmidt, D. H. Perlmutter Am J Physiol 289, G444 (2005).
9. N. Mizushima, T. Yoshimura Autophagy 3, 542 (2007).
10. J. A. Carlson et al J Clin Invest 82, 26 (1988).
11. J. A. Carlson et al J Clin Invest 83, 1193 (1989).
12. D. A. Rudnick et al. Hepatology 39, 1048 (2004).
13. J. H. Teckman et al Am J Physiol 286, G851 (2004).
14. J. H. Teckman et al Am J Physiol 279, G961 (2000).
15. J. H. Teckman, J. K. An, S. Loethen, D. H. Perlmutter Am J Physiol 283, G1156 (2003).
16. T. Hidvegi et al J Biol Chem 282, 27769 (2007).
17. S. Maeda et al. Immunity 19, 725 (2003).
18. S. Paranjpe et al. Hepatology 45, 1471 (2007).
19. C. H. Osterreicher et al. Hepatology 50, 185 (2009).
20. J. F. Woessner. Arch Biochem Biophys 93, 440 (1961).
21. T. D. Oury, K. Thakker, J. D. Crapo, L. Y. Chang, B. J. Day. Am J Resp Cell Mol Biol 25, 164 (2001).
22. R. M. Stepanovi-Petrovic et al. Anesth Analg 106, 1897 (2008).
23. K. K. Borowicz et al. Psychopharm 195, 167 (2007).
24. M. Harada, S. Hanada, D. M. Toivola, N. Ghori, M. B. Omary. Hepatology 47, 2026 (2008).
25. D. H. Perlmutter, Cell Death Differ. 16, 39 (2009).
26. E. Piitulainen, J. A. Carlson, K. Ohlsson, T. Sveger, Chest 128, 2076 (2005).
27. Y. Wu et al., Proc. Natl. Acad. Sci. U.S.A. 91, 9014 (1994).
28. S. Pan et al., Hepatology 50, 275 (2009).
29. D. Qu, J. H. Teckman, S. Omura, D. H. Perlmutter, J. Biol. Chem. 271, 22791 (1996).
30. T. Kamimoto et al., J. Biol. Chem. 281, 4467 (2006).
31. K. B. Kruse, J. L. Brodsky, A. A. McCracken, Mol. Biol. Cell 17, 203 (2006).
32. C. M. Cabral, P. Choudhury, Y. Liu, R. N. Sifers, J. Biol. Chem. 275, 25015 (2000).
33. L. Zhang et al., Proc. Natl. Acad. Sci. U.S.A. 104, 19023 (2007).
34. B. Ravikumar, S. Sarkar, D. C. Rubinsztein, Methods Mol. Biol. 445, 195 (2008).
35. E. T. Powers, R. I. Morimoto, A. Dillin, J. W. Kelly, W. E. Balch, Annu. Rev. Biochem. 78, 959 (2009).
36. C. Haas and D. Selkoe, Nat. Rev. Mol. Cell Biol. 8, 101 (2007).
37. B. Boland et al., J. Neurosci. 28, 6926 (2008).
38. R. Nixon, J. Cell Sci. 120, 4081 (2007).
39. F. Pickford et al., J. Clin. Invest. 118, 2190 (2008).
40. E. Cohen et al., Cell 139, 1157 (2009).
41. T. Hidvegi et al., Science 329, 229 (published Jun. 3, 2010 online as DOI:10.1126/science.1190354 and in print on Jul. 9, 2010; see also online supplement.)
42. R. Sifers, Science 329, 154 (Jul. 9, 2010)
43. D. A. Lomas, D. L. Evans, J. J. Finch, R. W. Carrell. Nature 357, 605 (192).
44. J. K. Stoller, L. S. Aboussouan. Lancet 365, 2225 (2005).
45. M. J. Dycaico et al. Science 242, 1404 (1988).
46. E. D. Werner, J. L. Brodsky, A. A. McCracken. Proc Natl Acad Sci USA 26, 13797 (1996).
47. K. B. Kruse, J. L. Brodsky, A. A. McCracken. Mol Biol Cell 17, 203 (2006).
48. S. Sarkar et al. Nature Chem Biol 3, 331 (2007).
49. V. Kirkin, D. G. McEwan, I. Novak, I. Dikic. Molec Cell 34, 259 (2009).
50. P. O. Bauer et al. J Biol Chem 284, 13153 (2009).
51. N. Mizushima, B. Levine, A. M. Cuervo, D. J. Klionsky. Nature 451, 1069 (2008).
52. D. Naisbitt et al. Molec. Pharmacol. 63, 732 (2003).
53. M. Juruena et al. Prog. Neuro-Psycho. Biol. Psych. 33(1), 94 (2009).
54. A. Ambrósio et al. Eur. J. Pharmacol. 406, 191 (2000).
55. LA Holcomb et al., Behav. Genet. 29, 177 (1999).
56. M. Filali and R. Lalonde, Brain Res. 1292, 93 (2009).
57. A D Cohen et al., Lett. Drug. Des. Discov. 6, 437 (2009).
58. S M Grant, D Faulds, Drugs 43(6), 873 (1992).

Various publications are cited herein, the contents of which are hereby incorporated by reference in their entireties.

We claim:

1. A method of treating Alzheimer's Disease consisting essentially of administering, to a subject in need of such treatment, a therapeutically effective amount of carbamazepine or a carbamazepine-like compound selected from the group consisting of carbamazepine-10,11-epoxide, iminostilbene, dihydrocarbamazepine, ethyl urea, phenyl urea, diphenylurea, dicyclohexylurea, phenytoin, substituted and unsubstituted iminobenzyl compounds, imipramine, (S)-(-)-10-acetoxy-10,11-dihydro-5Hdibenz[b,f]azepine-5-carboxamide (BI 2-093), and 10,11-dihydro-10-hydroxyimino-5Hdibenz[b,f,]azepine-5-carboxamide (BIA 2-024).

2. The method of claim 1 where the carbamazepine-like compound is carbamazepine.

3. The method of claim 1 where the carbamazepine-like compound is oxcarbazepine.

4. The method of claim 1 where the carbamazepine-like compound is metabolized, in the subject, to form 10, 11-dihydro-10-hydroxy-carbamazepine.

* * * * *